(12) United States Patent
Cormier et al.

(10) Patent No.: US 8,039,459 B2
(45) Date of Patent: Oct. 18, 2011

(54) NICOTINIC RECEPTOR AGONISTS FOR THE TREATMENT OF INFLAMMATORY DISEASES

(75) Inventors: Yvon Cormier, Neuville (CA); Evelyne Israel-Assayag, Sainte-Foy (CA); Marie-Renée Blanchet, Ile d'Orléans (CA); René C. Gaudreault, St-Nicolas (CA); Philippe Labrie, Québec (CA)

(73) Assignee: Universite Laval, Quebec (CA)

( * ) Notice: Subject to any disclaimer, the term of this patent is extended or adjusted under 35 U.S.C. 154(b) by 822 days.

(21) Appl. No.: 11/632,051

(22) PCT Filed: Jul. 15, 2005

(86) PCT No.: PCT/CA2005/001120
§ 371 (c)(1),
(2), (4) Date: Apr. 16, 2008

(87) PCT Pub. No.: WO2006/005195
PCT Pub. Date: Jan. 19, 2006

(65) Prior Publication Data
US 2008/0221085 A1    Sep. 11, 2008

Related U.S. Application Data

(63) Continuation-in-part of application No. 10/890,987, filed on Jul. 15, 2004, now abandoned.

(51) Int. Cl.
*A61K 31/00* (2006.01)
*A01N 43/00* (2006.01)
(52) U.S. Cl. .................................. 514/211.08; 514/183
(58) Field of Classification Search .................. 514/183
See application file for complete search history.

(56) References Cited

U.S. PATENT DOCUMENTS

| | | | |
|---|---|---|---|
| 2,232,662 A | 2/1941 | Hockenyos et al. |
| 2,456,851 A | 12/1948 | Woodward et al. |
| 2,466,788 A | 4/1949 | Howard et al. |
| 2,524,094 A | 10/1950 | Howard et al. |
| 2,541,138 A | 2/1951 | Howard et al. |
| 2,778,772 A | 1/1957 | Chen |
| 2,507,925 A | 5/1960 | Niederl et al. |
| 3,071,509 A | 1/1963 | O'Neill |
| 3,402,039 A | 9/1968 | Mussell et al. |
| 4,220,781 A | 9/1980 | Sanders et al. |
| 4,321,387 A | 3/1982 | Chavdarian et al. |
| 5,227,391 A | 7/1993 | Caldwell et al. |
| 5,691,365 A | 11/1997 | Crooks et al. |
| 5,846,983 A | 12/1998 | Sandborn et al. |
| 5,977,144 A | 11/1999 | Meyer et al. |
| 5,981,549 A | 11/1999 | Viner |
| 6,177,429 B1 | 1/2001 | Sit et al. |
| 6,610,713 B2 | 8/2003 | Tracey |
| 6,838,471 B2 | 1/2005 | Tracey |
| 7,067,672 B2 | 6/2006 | Comins et al. |
| 7,091,357 B2 | 8/2006 | Crooks et al. |
| 7,186,277 B2 * | 3/2007 | Genet et al. ..................... 8/405 |
| 7,501,520 B2 | 3/2009 | Comins et al. |
| 2002/0160988 A1 | 10/2002 | Amitai et al. |
| 2004/0116519 A1 | 6/2004 | Slatter |
| 2004/0132737 A1* | 7/2004 | Cormier et al. .......... 514/252.12 |
| 2004/0132774 A1 | 7/2004 | Heath |
| 2004/0138289 A1 | 7/2004 | Richards et al. |
| 2004/0242569 A1 | 12/2004 | Lennon |
| 2004/0254373 A1 | 12/2004 | Piotrowski et al. |
| 2005/0019271 A1 | 1/2005 | Bannister et al. |
| 2005/0075323 A1 | 4/2005 | Day et al. |
| 2005/0130990 A1 | 6/2005 | Cormier et al. |
| 2009/0197921 A1 | 8/2009 | Solis Herrera |

FOREIGN PATENT DOCUMENTS

| | | |
|---|---|---|
| JP | 2003/176240 A | 6/2003 |
| WO | WO 96/15117 | 5/1996 |
| WO | WO 98/02188 | 1/1998 |
| WO | WO/99/21834 | 5/1999 |
| WO | WO 00/23062 | 4/2000 |
| WO | WO 01/15697 A | 9/2000 |
| WO | WO 02/44176 A1 | 6/2002 |
| WO | WO/02/076434 | 10/2002 |
| WO | WO/2006/005195 | 1/2006 |

OTHER PUBLICATIONS

Adelowo-Imeokparia et al., Effects of Phenyl Ring Substituents on the Fungicidal Activity of O-Ethyl-n-Phenyl Carbamate, 2008, World Journal of Agricultural Sciences, vol. 4, No. 1, pp. 48-52.*
Zanger et al., Remingtons Pharmaceutical Sciences, 1980, Chapter 27, pp. 420-435.*
Thompson, D. C. et al., *Nicotinic Agonist Modulation of Feline Bronchomotor Tone*, Clinical and Experimental Pharmacology and Physiology, vol. 17, No. 2, 1990, pp. 83-97.
Nielsen et al., 2000, *Novel Potent Ligands for the Central Nicotinic Acetylcholine Receptor: Synthesis, Receptor Binding and 3D-QSAR Analysis*, J. Med. Chem. 43, 2217-2226.
Romanelli et al., 2001, *Structure-Affinity Relationships of a Unique Nicotinic Ligand: $N^1$-Dimethyl-$N^4$-phenylpiperazinium Iodide (DMPP)*, J. Med. Chem. 44, 3946-3955.
Toma et al., 2002, *6-Chloropyridazin-3-yl Derivatives Active as Nicotinic Agents: Synthesis, Binding and Modeling Studies*, J. Med. Chem. 45, 4011-4017.
Manetti et al., 1999, *Hybridized and Isosteric Analogues of $N^1$-Acetyl-$N^4$-dimethyl-piperazinium Iodide (ADMP) and $N^1$-Phenyl-$N^4$-dimethyl-piperazinium Iodide (DMPP) with Central Nicotinic Action*, Bioorganic & Medicinal Chemistry 7, 457-465.
Guandalini et al., 2005, *Rigid analogs of DMPP as probes for the nicotinic receptors*, IL Farmaco 60, 99-104.
Hanson, R. N., 1983, *Preparation and Evaluation of Radioiodinated Phenylpiperazines as Adrenomedullary Imaging Agents*, Int. J. Nucl. Med. Biol. 10(4): 219-222.
Zilber, A.P., *Respiratory Failure*, Moscow "Meditsina", 1989, pp. 288-289 and 295-296.

(Continued)

Primary Examiner — Jeffrey S Lundgren
Assistant Examiner — Meghan Finn
(74) Attorney, Agent, or Firm — Buchanan Ingersoll & Rooney PC

(57) ABSTRACT

Nicotine receptor agonists or analogs or derivatives thereof for treating inflammatory pulmonary diseases, and pharmaceutical compositions including nicotine receptor agonists or analogs or derivatives thereof. Compounds of formula wherein R1, R2, Xa and Ya are as defined herein are also provided.

1 Claim, 20 Drawing Sheets

OTHER PUBLICATIONS

Berkow, R., Guide to Medicine, vol. 1, Moscow, "MIR", 1997, pp. 450-451.
Reynold A. Panettieri, Jr., *Chronic Obstructive Lung Disease*, Pathophysiology of Lungs, Moscow, "BINOM", 2001, pp. 95-98.
Beleslin et al., *Central Nicotinic Receptors: Vomiting, Ear Twitching and Panting*, Brain Res. Bull., vol. 11, No. 3, pp. 299-302, 1983.
Chemical Abstracts, Registry No. 54-77-3, 1971.
Flenley, D.C., *New drugs in respiratory disorders: I.*, Br. Med. J. (Clin. Res. Ed.), Mar. 12, 1983; 286(6368): 871-875.
Becker, A.B. et al., *The bronchodilator effects and pharmacokinetics of caffeine in asthma*, N. Engl. J. Med., Mar. 22, 1984; 310(12); 743-6.
Baldassarre, Sandra et al., *Asthma attacks induced by low doses of celecoxib, aspirin and acetaminophen.*, J. Allergy and Clin. Immunol. 2006, 117(1): 215-217.
Etter, J.-F., *Cytisine for Smoking Cessation*: A Literature Review and a Meta-analysis. Arch. Intern. Med., Aug. 14-28, 2006; 166(15): 1553-9.
Wang et al., *Interferon gamma Induction of Pulmonary Emphysema in the Adult Murine Lung*, J. of Experimental Medicine, vol. 192, No. 11, Dec. 4, 2000, pp. 1587-1599 (XP-002257504).
Database WPI Derwent publication Ltd. London, GB; Abstract Only Considered, An 2000-291290 antiasthmatic drug as tablet and a method of tablet preparation & RU 2 127 123 A. (MOSC, Chem-Pharm PRODM Assoc) Mar. 10, 1999.
Fernandez, Elizabeth and Craviso, Gale L., *Protein Synthesis Blockade Differentially Affects the Degradation of Constitutive and Nicotinic Receptor-Induced Tyrosine Hydroxylase Protein Level in Isolated Bovine Chromaffin Cells*, Journal of Neurochemistry, vol. 73, No. 1, 1999, pp. 169-178.
Cormier, Y. et al., 1985, *Factors influencing the development of serum precipitins to farmer's lung antigen in Quebec dairy farmers*. Thorax 40(2): 138-142.
Cormier, Y. et al., 1988, *Sequential bronchoalveolar lavage in experimental extrinsic allergic alveolitis. The influence of cigarette smoking*, Am Rev Respir Dis 137(5): 1104-1109.
Cormier, Y. et al., 1998, *Hypersensitivity pneumonitis in peat moss processing plant workers*, Am J Respir. Crit Care Med 158(2): 412-417.
Gariepy, L. et al., 1989, *Predictive value of bronchoalveolar lavage cells and serum precipitins in asymptomatic dairy farmers*, Am Rev Respir. Dis. 140(5):1386-1389.
Lawrence, E.G. et al., 1986, *Cigarette smoking and bronchoalveolar T Cell populations in sarcoidosis*, Ann NY Acad Sci 465:657-664.
Valeyre D. et al., 1988, *Smoking and pulmonary sarcoidosis: effect of cigarette smoking on prevalence, clinical manifestations, alveolitis, and evolution of the disease*, Thorax 43(7):516-524.
Rubin, D.T. and Hanuer, S. B., 2000, *Smoking and inflammatory bowel disease*. Eur J Gastroenterol Hepetol 12(8):855-862.
Thomas, G.A. et al., 2000, *Role of smoking in inflammatory bowel disease: implications for therapy*. Postgrad Med J 76(895):273-279.
Guslandi, M., 1999, *Nicotine Treatment for ulcerative colitis*. Br. . Clin Pharmacol 48(4):481-484.
Guslandi, M., 1999, *Long-term effects of a single course of nicotine treatment in acute ulcerative colitis:remission maintenance in a 12-month follow-up study*. Int J Colorectal Dis 14(4-5):261-262.
Rezvani, A.H. and Levin E.D., 2001, *Cognitive effects of nicotine*. Biol Psychiatry 49(3):258-267.
Kelton, M.C. et al., 2000, *The effects of nicotine in Parkinson's disease*. Brain Cogn 43(1-3):274-282.
Bertram, K.G., 1998, *Basic and clinical pharmacology*. Editions Appetton and Lange. Stanford. Connecticut.
Sekhon, H.S. et al., 1999, *Prenatal nicotine increases pulmonary alpha 7 nicotinic receptor expression and alters feta lung development in monkeys*. J Clin Invesst 103(5):637-647.
Maus, A.D. et al., 1998, *Human and rodent bronchial epithelial cells express functional nicotinic acetylcholine receptors*, Mol Pharmacol 54(5):779-788.
Shriver, S.P. et al., 2000, *Sex-specific expression of gastrin-releasing peptide receptor .\* relationship to smoking history and risk of lung cancer*. J Nati Cancer Inst. 92(1):24-33.

Ferguson, D.G. et al., 2000, *The alpha3 subtype of the nicotinic acetylcholine receptor is expressed in airway-related neurons of the nucleus tractus solitarius, but is not essential for reflex bronchoconstn'ction in ferrets*. Neurosci Lett 287(2):141-145.
Singh, S.P. et al., 2000, *Acute and chronic nicotine exposures modulate the immune system through different pathways*. Toxicol Appl Pharmacol 164(1): 65-72.
Kalra, R. et al., 2000, *Effects of cigarette smoke on immune response:chronic exposure to cigarette smoke impairs antigen-mediated signaling in T cells and depletes IP3-sensitive Ca(2+) stores*. J Pharmacol Exp Ther 293(1):166-171.
Sugano, N. et al., 1998, *Nicotine inhibits the production of inflammatory mediators in U937 cells through modulation of nuclear factor-kappaB activation,*. Biochem Biophys Res Commun 252(1):25-28.
Yates, S.L. et al., 1995, *Up-regulation of nicotinic acetycholine receptors following chronic exposure of rats to mainstream cigarette smoke or alpha 4 beta 2 receptors to nicotine*. Biochem Pharmacol 50(12):2001-2008.
Sopori, M.L. and Kosak W., 1998, *Immunomodulatory effects of cigarette smoke*. J Neuroimmunol 83(1-2):148-156.
Lahmouzi, J. et al., 2000, *Effect of nicotine on rat gingival fibroblasts in vitro*. Connect Tissue Res 41(1):69-80.
Geng, Y. et al., 1996, *Effects of nicotine on the immune response. II. Chronic nicotine treatment induces T cell anergy,*. J Immunol 156(7):2384-2390.
McCrea, K.A. et al., 1994, *Altered cytokine regulation in the lungs of cigarette smokers*, Am J Respir Crit Care Med 150(3):696-703.
Ohta, T. et al., 1998, *Cigarette smoking decreases interleukin-8 secretion by human alveolar macrophages*, Respir. Med. 92(7):922-7.
Suzuki, N. et al., 1999, *Effects of cigarette smoking on Fas/Fas ligand expression of human lymphocytes*. Cell Immunol 192(1):48-53.
Zia, S. et al., 1997, *Nicotine enhances expression of the alpha 3, alpha 4, alpha 5; and alpha 7 nicotinic receptors modulating calcium metabolism and regulating adhesion and motility of respiratoty epithelial cells,*. Res Commun Mol Pathol Pharmacol 97(3):243-262.
Zhang, S. and Petro T.M., 1996, *The effects of nicotine on murine CD4 T cell responses*. Int J Immunopharmaco118(8-9):467-478.
Bugeon, L and Dallman J., 2000, *Costimulation of T cells*. Am J Respir Crit Care Med 162(4 Pt 2): S164-168.
Green, J.M., 2000, *The B7/CD28/CTL,44 T-cell activation pathway. Implications for inflammatory lung disease*. Am. J. Respir. Cell. Mol. Biol. 22(3):261-264.
Lenschow, D.J. et al., 1996, *CD28/B7 system of T cell costimulation*. Annu Rev. Immunol. 14:233-258.
Walunas, T.L. and Bluestone J.A., 1998, *CTLA-4 regulates tolerance induction and T cell differentiation in vivo*. J Immunol 160(8):3855-3860.
Walunas, T.L. et al., 1994, *CTLA-4 can function as a negative regulator of T cell activation*. Immunity 1(5):405-413.
Israel-Assayag, E. et al., 1999, *Expression of costimulatory molecules on alveolar macrophages in hypersensitivity pneumonitis*, Am J Respir Crit Care Med 159(6): 1830-1834.
Israel-Assayag E. et al., 1999, *Blockade of T cell constimulation by CTL44-Ig inhibits lung inflammation in murine hypersensitivity pneumonitis*, J Immunol 163(12): 6794-6799.
Larche, M. et al., 1998, *Costimulation throuth CD86 is involved in airwat antigen-presenting cell and T cell responses to allergen in atopic asthmatics*, J Immunol 161(11):6375-6382.
Mathur, M. et al., 1999, *CD28 interactions with either CD80 or CD86 are sufficient to induce allergic airway inflammation in mice*. Am J Respir Cell Mol Biol 21(4):498-509.
Nicod, L.P. and Isler, P., 1997, *Alveolar macrophages in sarcoidosis coexpress high levels of CD86 (87.2), CD40, and CD3OL*. Am J Respir Cell Mol Biol 17(1):91-6.
Kesingland, A.C. et al., 2000, *Analgesic profile of the nicotinic acetylcholine receptor agonists, (+)-epibatidine and ABT-594 in models of persistent inflammatory and neuropathic pain*, Pain 86(1-2):113-118.
Mellon, R.D. and Bayer B.M., 1999, *The effets of morphine, nicotine and epibatidine on lymphocyte activity and hypothalamic-pituitary-adrenal axis responses*, J Pharmacol Exp Ther 288(2):635-642.

Yokotani, K. et al., 2000, *Characterization of nicotinic acetylcholine receptor-mediated noradrenaline release from the isolated rat stomach*, Eur J Pharmacol 402(3):223-9.

Yost, C.S. and Winegar B.D., 1997, *Potency of agonists and competitive antagonists on adult-and-fetal-type nicotinic acetylcholine receptors*, Cell Mol Neurobiol 17(1):35-50.

Fecho, K. et al., 1993, *Alterations of immune status induced by the sympathetic nervoux syatem: immunomodulatory effects of DMPP alone and in combination with morphine*, Brain Behav. Immun 7(3): 253-270.

Thompson D. et al., 1990, *Nicotinic agonist modulation of feline bronchomotor tone*, Clin Exp Pharmacol Physiol 17(2):83-97.

Barnes, P.J., 2001, *Future Advances in COPD Therapy*, Respiration 68(5): 441-448.

Lasky J.A. and Ortiz, L.A., 2001, *Antifibrotic therapy for the treatment of pulmonary fibrosis*, Am J Med Sci 322(4): 213-221.

Baron P.J., 1996, *Beneficial effecos of nicotine and cigarette smoking: the real, the possible and the spurious*, Br Med Bull 52(1): 58-73.

Waldum, H.L. et al., 1996, *Long-term effects of inhaled nicotine*, Life Sci 58(16) 1339-1346.

Warren, C.P., 1977, *Extrinsic allergic alveolitis: a disease commoner in non-smokers*, Thorax 32(5): 567-569.

Cormier, Y. et al., 1994, *Long-tenn viral enhancement of lung response to Saccharopolyspora rectivirgula*, Am J Respir Crit Care Med 149(2 Pt1):490-494.

Gudmundsson, G and Hunninghake G.W., 1997, *Interferon-gamma is necessary for the expression of hypersensitivity pneumonitis*, J Clin Invest 99(10):2386-2390.

Denis, M. et al., 1993, *A Study of monokine release and natural killer activity in the bronchoalveolar lavage of subjects with farmer's lung*, Am Rev Respir Dis 147(4): 934-939.

Wahlstrom, J.K. et al., 2001, *Analysis of intracellular cycokines in CD4(+) and CD8(+) lung and blood T cells in sarcoidosis*, Am J Respir Crit Care Med 163(1): 115-121.

Cohn, L. et al., 2001, *IL-4 promotes airway eosinophilia by suppressiong IFN-gamma production: definnin a novel role for IFN-gamma in the regulation of allergic airway inflammation*, J Immunol 166(4):2760-2767.

Laliberte, R. et al., 2001, *Decreased capacity of asthmatic bronchial fibroblasts to degrade collagen*, Matrix Biol Jan 19(8): 743-753.

Boulet, L.P. et al., 2000, *Airway hyperresponsiveness, inflammation, and subepithelial collagen deposition in recently diagnosed versus long-standing mild asthma. Influence of inhalend corticosteroids*, Am J Respir Crit Care Med 162 (4 Pt 1):1308-1313.

Dempsey, O.J., 2000, *Leukotriene receptor antagonist therapy*, Postgrad Med J 76(902): 767-773.

Busse, W.W., 1998, *Leukotrienes and inflammation*, Am J Respir Crit Care Med 157 (6Pt) 2: S210-213.

Zisman, D.A. et al., 2000, *Cyclophosphamide in the treatment of idiopathic pulmonary fibrosis: a prospective study in patients who failed to respond to corticosteroids*, Chest 117(6): 1619-1626.

Redington, A.E., 2000, *Fibrosis and airway remodeling*, Clin Exp Allergy 30 Suppl 1: 42-45.

Frew, A.J. and Plummeridge, M.J., 2001, *Alternative agents in asthma*, J Allergy Clin Immunol 108(1): 3-10.

Migueres et al., 1986, *Techniques of Desensitization*, Revue des Maladies Respiratories, 3(1):39-44, abstract.

International Preliminary Report on Patentability issued Jan. 16, 2007 in corresponding PCT/CA2005/001120.

Written Opinion issued Oct. 12, 2005 in corresponding PCT/CA2005/001120.

Traynor, "Epibatidine and pain", British Journal of Anaesthesia, 1998, pp. 69-76.

Tønder et al., "An improved nicotinic pharmacophore and a stereoselective CoMFA-model for nicotinic agonists acting at the central nicotinic acetylcholine receptors labelled by [$^3$H]-N-methylcarbamylcholine", Journal of Computer-Aided Molecular Design, 2001, pp. 247-258.

Supplementary European Search Report dated Sep. 10, 2009 in corresponding EP 05764252.2-2101/1773779.

Green et al., Br. "Nicotinic Stimulant Action of Some Tolyl and Xylyl Analogues of 1,1-dimethyl-4-phenylpiperazinium (DMPP)" *J. Pharmac.* (1971) 43:370-378.

\* cited by examiner

\* = p < 0.05 compared to SR group

* = p < 0.005

* = p < 0.05

NICOTINIC RECEPTOR AGONISTS FOR THE TREATMENT OF INFLAMMATORY DISEASES

CROSS-REFERENCE TO RELATED APPLICATIONS

This application is a National Stage application of PCT/CA2005/001120, filed on Jul. 15, 2005, which is a continuation-in-part of Ser. No. 10/890,987 filed Jul. 15, 2004 now abandoned, the entire content of which are hereby incorporated by reference.

BACKGROUND OF THE INVENTION a) Field of the Invention

The present invention relates to the treatment of inflammatory diseases, including a variety of pulmonary diseases, through the use or administration of nicotinic receptor agonists or analogs and derivatives thereof.

b) Description of Prior Art

Although a normal man or woman breathes more than one cubic meter of air every hour, our lung defense mechanisms usually deal with the large quantities of particles, antigens, infectious agents and toxic gases and fumes that are present in inhaled air. The interaction of these particles with the immune system and other lung defense mechanisms results in the generation of a controlled inflammatory response which is usually protective and beneficial. In general, this process regulates itself in order to preserve the integrity of the airway and alveolar epithelial surfaces where gas exchange occurs. In some cases, however, the inflammatory response cannot be regulated and the potential for tissue injury is increased. Depending on the type of environmental exposure, genetic predisposition, and a variety of ill-defined factors, abnormally large numbers of inflammatory cells can be recruited at different sites of the respiratory system, resulting in illness or disease.

The inflammatory response to inhaled or intrinsic stimuli is characterized by a non-specific increase in the vascular permeability, the release of inflammatory and chemotactic mediators including histamine, eicosanoids, prostaglandins, cytokines and chemokines. These mediators modulate the expression and engagement of leukocyte-endothelium cell adhesion molecules allowing the recruitment of inflammatory cells present in blood.

A more specific inflammatory reaction involves the recognition and the mounting of an exacerbated, specific immune response to inhaled antigens. This reaction is involved in the development of asthma, hypersensitivity pneumonitis (HP) and possibly sarcoidosis. Dysregulation in the repair mechanisms following lung injury may contribute to fibrosis and loss of function in asthma, pulmonary fibrosis, chronic obstructive pulmonary disease (COPD), and chronic HP.

It was previously reported that the incidence of HP is much lower among current smokers than in non-smokers (1-4). Sarcoidosis is also less frequent in smokers than in non smokers (5, 6). The mechanisms underlying the beneficial effects of cigarette smoking on the development of HP and other inflammatory diseases are still unknown but may be linked to the immunomodulatory effect of nicotine. There are clinical observations of asthma de novo or exacerbation after smoking cessation. Proof of this is difficult to obtain and any protective effects of nicotine in the prevention or treatment of asthma are likely overwhelmed by the negative effects of tobacco smoke with its thousands of constituents.

The protective effect of smoking has also been reported in other diseases, the most studied being ulcerative colitis, an inflammatory intestinal disease (7, 8). Nicotine has been successfully used in the treatment of this disease (9, 10). Other studies have looked at the possible therapeutic value of nicotine in the treatment of Alzheimer's disease and Parkinson's disease. (11, 12).

Nicotinic receptors are pentamers made up of five polypeptide subunits which act as ligand-gated ions channels. When the ligand binds to the receptor, a conformational change in the polypeptide occurs, opening a central channel that allows sodium ion to move from the extracellular fluid into the cytoplasm. Four types of subunits have been identified: $\alpha$, $\beta$, $\gamma$ and $\delta$. The receptor can consist of any combination of these four types of subunits (13). Recent work has shown that alveolar macrophages (AM) can express the $\alpha$-7 subunit (14), while bronchial epithelial cells express the $\alpha$-3, $\alpha$-5 and $\alpha$-7 subunits (15), and lymphocytes the $\alpha$-2, $\alpha$-5, $\alpha$-7, $\beta$-2 and $\beta$-4 subunits (14). Fibroblasts (16) and airway smooth muscles cells (17) also express these receptors. Therefore, resident pulmonary cells (AM, dendritic cells, epithelial cells, fibroblasts, etc.) and those recruited in inflammatory diseases (lymphocytes, polymorphonuclear cells) express nicotinic receptors.

Nicotinic receptor activation in lymphocytes affects the intracellular signalization, leading to incomplete activation of the cell. In fact, nicotine treatment upregulates protein kinase activity, which in turn upregulates phospholipase A2 (PLA2) activity. PLA2 is responsible for cleaving phosphoinositol-2-phosphate (PIP2) into inositol-3-phosphate (IP3) and diacylglycerol (DAG) (18, 19). The continuous presence of IP3 in the cell would appear to result in the desensitization of calcium stores, leading to their depletion (19). This observation could explain the fact that nicotine-treated lymphocytes do not release enough calcium into the cytoplasm to activate transcription factors such as NFk-B (20).

Nicotine, the major pharmacological component of cigarette smoke, is one of the best known nicotinic receptor agonists (21). This natural substance has well defined anti-inflammatory and immunosuppressive properties (22), and may have anti-fibrotic properties (23). Exposure of animals to smoke from cigarettes with high levels of nicotine is more immunosuppressive than that from low-nicotine cigarettes (24). Moreover, treatment of rats with nicotine inhibits the specific antibody response to antigens and induces T cell anergy (25). Although they are increased in number, AM from smokers show a decreased ability to secrete inflammatory cytokines in response to endotoxins ((20, 25, 26)) and nicotine seems to be the responsible component of this inhibition (26). One study also showed that peripheral blood lymphocytes from smokers express higher levels of FAS ligand (FASL) and that nicotine increases FASL expression on lymphocytes from non-smokers, indicating that nicotine may affect cell apoptosis (27). Nicotine was also shown to have an inhibitory effect on the proliferation and extracellular matrix production of human gingival fibroblasts in vitro (23). Of interest, nicotine treatment seems to up-regulate the expression of nicotinic receptors (28). Nicotine itself is a safe substance that does not seem to have any long term side effects (48-49). Smoke-related diseases of the lungs, heart and arteries are not caused by nicotine but by the thousands of other chemicals present in the inhaled smoke. The main problem is that nicotine crosses the blood-brain barrier, inducing addiction. The harmful effects of cigarette smoking are obvious. Although nicotine is not responsible for the toxic effects of cigarette smoking, the association remains.

Nicotinic agonists may down-regulate T cell activation, indeed, nicotine has been shown to affect T cell expression of the co-stimulatory molecules CD28 and CTLA4 (29).

The B7/CD28/CTLA4 co-stimulatory pathway plays a key regulatory role in T-cell activation and homeostasis (30, 31). Two signaling pathways are involved. A positive signal involves the engagement of B7 (CD80/CD86) molecules with T cell CD28 receptors which results in the potentiation of T cell responses (proliferation, activation, cytokine expression, and survival) (32). A negative signal involves B7 interactions with CTLA4 on activated T cells, leading to a downmodulation of T cell responses (33, 34). The balance between CD28 and CTLA4 derived signals may alter the outcome of T-cell activation.

In HP, it was previously reported that an upregulation of B7 molecule expression on AM in patients with active HP (35) and in murine HP (36). It was also shown that a blockade of the B7-CD28 co-stimulatory pathway in mice inhibited lung inflammation (36). These results also demonstrated that the expression of B7 molecules on AM is lower in smokers than in non-smokers and that an in vitro influenza virus infection is able to upregulate B7 expression in normal human AM but not in AM from smokers; whether this is due to nicotine or other substances present in cigarette smoke is unknown (35). An up-regulation of the B7 molecules has also been reported in asthma (37, 38) and sarcoidosis (39).

Epibatidine is the most potent nicotinic agonist known so far (40). It has anti-inflammatory and analgesic properties. In fact, its analgesic potential is two hundred times that of morphine (40). This molecule is also known to inhibit lymphocyte proliferation in vitro (41). The binding of epibatidine to the receptor is non-specific (42). Unfortunately, epibatidine has major toxic side effects mostly on the cardiovascular and the central nervous systems making it inappropriate for use as an anti-inflammatory drug to treat pulmonary diseases (40).

Dimethylphenylpiperazinium (DMPP) is a synthetic nicotinic agonist that is non-specific (13). Its potency for the receptor is about the same as nicotine, depending on the kind of cells implicated in the stimulation (43). Its advantage over nicotine and other nicotinic agonists is that its chemical configuration prevents it from crossing the blood-brain barrier, thus causing no addiction or other central nervous effects (13). The anti-inflammatory properties of DMPP are not well described. However, it has been shown that a chronic in vivo treatment could decrease the number of white, blood cells, decrease the cytokine production by splenocytes and decrease the activity of natural killer cells (44). The effect of DMPP on airway smooth muscle cells has also been tested. DMPP has an initial short contractive effect which is followed by a relaxing effect when the cells are in contact with the agonist for a longer period of time (45). This bronchodilatory effect may not necessarily in itself make DMPP the most useful treatment of asthma, since other potent bronchodilators are currently available on the market (82 agonists). However, the properties of this nicotinic receptor agonist are important since this drug could be safely administered to asthmatics and COPD patients for its anti-inflammatory properties. Moreover, there is no apparent evidence that DMPP has any toxic effect on major organs such as the heart, the brain, the liver or the lungs.

Corticosteroids are potent anti-inflammatory drugs. Their systemic use causes major side effects that preclude their long-term uses whenever possible. Inhaled poorly absorbed steroids are useful to treat airway inflammation. At low doses these drugs have little or no side effects. However, higher doses increase the risks for oral candidasis, vocal cords paralysis, cataracts and osteoporosis. Inhaled steroids have no effects on lung interstitium and have no anti-fibrotic properties (57)

More recent drugs, such as anti-leukotrienes, are useful in some asthmatics (58) but have no effects in COPD and other lung diseases. These drugs have anti-inflammatory properties limited to the components of inflammation caused by leukotrienes (59). The treatment of interstitial lung disease such as IPF, Sarcoidosis, HP, and BOOP basically rests on the use of systemic corticosteroids. This treatment is effective in controlling some of the inflammation but unfortunately induces serious side effects and does not reverse underlying fibrotic changes. Immunosupressive agents such as cyclophosphamide and azathioprine are sometimes tried in severe IPF but their therapeutic values are unproven and at most, very limited (60): In essence, lung fibrosis is usually progressive and untreatable, with most IPF patients dying of this condition (61).

Despite advances in the treatment of inflammatory illnesses, including pulmonary inflammatory diseases, treatment using available drugs or agents frequently results in undesirable side effects. For example, the inflammation of COPD is apparently resistant to corticosteroids, and consequently the need for the development of new anti-inflammatory drugs to treat this condition has been recognized (46).

Similarly, while corticosteroids and other immunosuppressive medications have been routinely employed to treat pulmonary fibrosis, they have demonstrated only marginal efficacy (47).

There is thus a need for new and reliable methods of treating inflammatory diseases, including pulmonary inflammatory diseases, in a manner that alleviates their symptoms without causing side effects.

SUMMARY OF THE INVENTION

In accordance with the present invention, there is provided a novel method for treating inflammatory diseases. Specifically, a novel method is described for treating pulmonary inflammatory diseases through the use or administration of an agent that binds to or modulates the function nicotinic receptor, such as nicotinic receptor agonists or analogues or derivatives thereof.

In one aspect, there is therefore provided a method for treating or preventing pulmonary inflammatory diseases comprising administering an effective amount of a compound that modulates the function of nicotinic receptors.

In a further aspect, there is also provided compounds of formula:

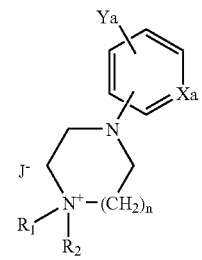

wherein $R_1$ and $R_2$ are independently lower alkyl of 1 to 10 carbon atoms,

Xa is CH or N,

Ya is one or more substituent selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 6 carbon atoms, alkoxy of 1 to 6 carbon atoms, alkylthio of 1 to 6 carbon atoms, alkylamino of 1 to 6 carbon atoms, alkanol of 1 to 6 carbon atoms, aralkyl, aryl of 6 to 10 carbon atoms and 3 to 10 membered heterocycle n is an integer from 0 to 2, J is a counter ion.

In still a further aspect, there is provided a pharmaceutical composition for treating pulmonary inflammatory diseases comprising a nicotinic receptor agonist and a pharmaceutically acceptable excipient.

In a further aspect, there is provided a method for inducing airways smooth muscle relaxation comprising administering an effective amount of a compound having the formula:

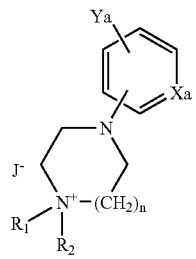

wherein $R_1$, $R_2$, Xa, Ya and J are as described herein.

In another aspect, there is provided by the present invention a method for inducing agonistic response in a pulmonary cell nicotinic receptor, comprising administering an effective amount of a nicotinic receptor agonist.

BRIEF DESCRIPTION OF THE DRAWINGS

The invention is illustrated but is not limited by the annexed drawings, in which.

DESCRIPTION OF PREFERRED EMBODIMENTS

Figure 1:
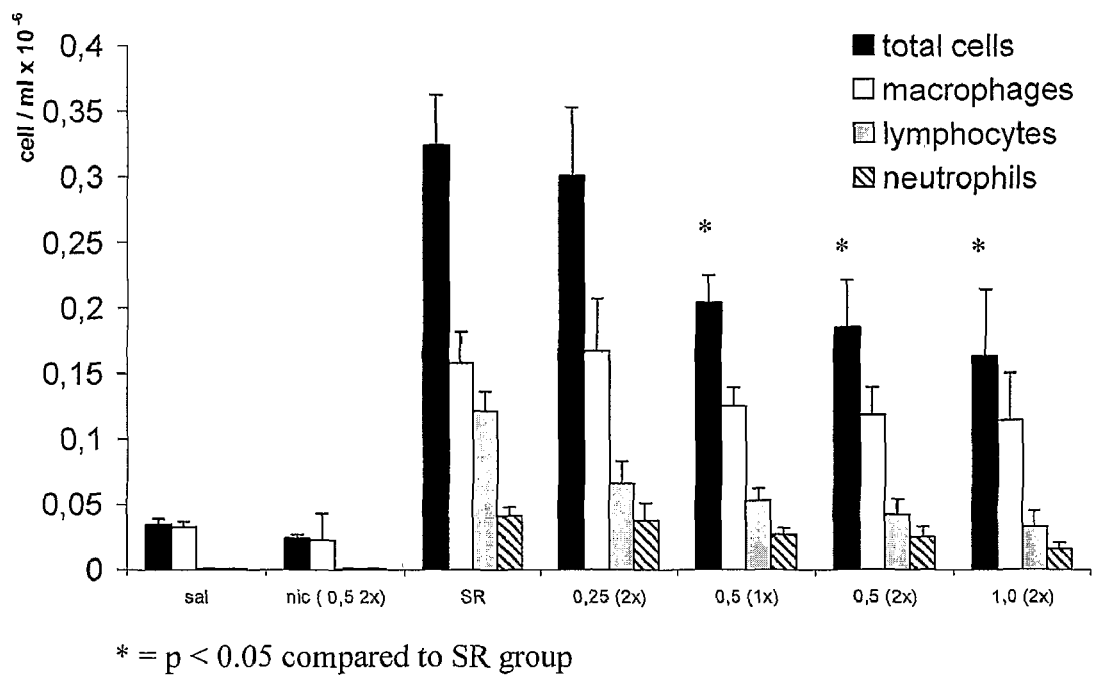
FIG. 1 shows total and differential cell counts in BAL cells.

Other objects, advantages and features of the present invention will become more apparent upon reading the following non-restrictive description of preferred embodiments thereof, given by way of example, only with reference to the accompanying drawings.

The idea of using nicotine or other nicotinic receptor agonists or analogs or derivatives thereof to treat inflammatory pulmonary disease is novel. Despite the impressive anti-inflammatory and immunosuppressive properties of nicotine and other nicotinic receptor agonists or analogs or derivatives, their usefulness in the treatment of allergic and other inflammatory lung diseases has not previously been disclosed. The drawbacks associated with cigarette are major reasons for the lack of prior interest in nicotinic agonists or analogs or derivatives thereof in the treatment of lung diseases.

The present invention thus proposes the of use nicotinic receptor agonists, such as DMPP and analogs as well as derivatives thereof, to treat inflammatory lung diseases such as asthma, COPD, interstitial pulmonary fibrosis (IPF), sarcoidosis, HP, and bronchiolitis obliterans with organizing pneumonitis (BOOP). The drug could be administered orally or, depending on the specific diseases or conditions, by targeted delivery directly to the lung by aerosolisation with different and preferred vehicles in order to minimize systemic effects.

The anti-inflammatory, immunosuppressive and/or bronchodilating properties, as well as minimal side effects of nicotinic receptor agonists and analogs and derivatives thereof, make these drugs ideally suited for medical use in the treatment of a large variety of lung diseases that are characterized by bronchial or interstitial inflammation. These diseases include diseases such as asthma, COPD, IPF, sarcoidosis, HP and BOOP.

In accordance with one embodiment, the invention provides a method for treating or preventing pulmonary inflammatory diseases comprising administering an effective amount of a compound that modulates the function of nicotinic receptors.

In one embodiment, the method is useful for treating pulmonary inflammatory diseases.

In one embodiment, the compound for use in the method of the invention is a nicotinic receptor agonist.

In one embodiment, the nicotinic receptor agonists is selected from the group consisting of dimethylphenylpiperazinium (DMPP), nicotine, epibatidine, cytisine, acetylcholine, and analogs thereof.

In another embodiment, the compounds for use in the method of the invention are:
i) a compound having the formula:

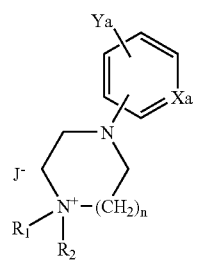

wherein $R_1$ and $R_2$ are independently lower alkyl of 1 to 10 carbon atoms,
Xa is CH or N,
Ya is one or more substituent selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 6 carbon atoms, alkoxy of 1 to 6 carbon atoms, alkylthio of 1 to 6 carbon atoms, alkylamino of 1 to 6 carbon atoms, alkanol of 1 to 6 carbon atoms, aralkyl, aryl of 6 to 10 carbon atoms and 3 to 10 membered heterocycle
n is an integer from 0 to 2,
J is a counter ion;
or ii) a compound having the formula:

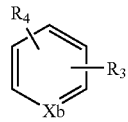

wherein $R_3$ is selected from

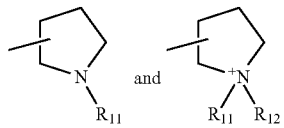

Xb is N or $N^+$—$R_{10}$,
$R_4$ is one or more substituent selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 10 carbon atoms, alkoxy of 1 to 10 carbon atoms, alkylthio of 1 to 10 carbon atoms, alkylamino of 1 to 10 carbon atoms, alkanol of 1 to 10 carbon atoms, aralkyl, aryl of 6 to 10 carbon atoms;
each of $R_{10}$, $R_{11}$ and $R_{12}$ are independently alkyl of 1 to 10 carbon atoms,
provided that a counterion is present when Xb is $N^+$—$R_{10}$;
or iii) a compound having the formula:

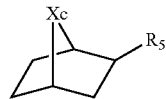

wherein Xc is $NR_{13}$ or $N^+$—$R_{13}R_{14}$, wherein $R_{13}$ and $R_{14}$ are independently alkyl of 1 to 10 carbon atoms,
$R_5$ is a 3 to 10 membered heterocycle,
provided that a counterion is present when Xc is $N^+$—$R_{13}R_{14}$;
or iv) a compound having the formula:

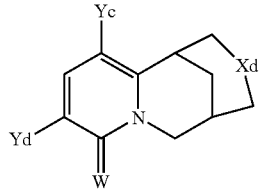

wherein W is O or S;
each of Yc and Yd are independently selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 10 carbon atoms, alkoxy of 1 to 10 carbon atoms, alkylthio of 1 to 10 carbon atoms, alkylamino of 1 to 10 carbon atoms, alkanol of 1 to 10 carbon atoms, aralkyl, aryl of 6 to 10 carbon atoms;

wherein Xd is $NR_{15}$ or $N^+—R_{15}R_{16}$, wherein $R_{15}$ and $R_{16}$ are independently alkyl of 1 to 10 carbon atoms, provided that a counterion is present when Xd is $N^+—R_{15}R_{16}$.

In a further embodiment, the compound useful in the method of the invention has the formula:

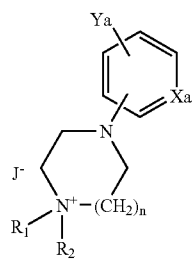

wherein $R_1$ and $R_2$ are independently alkyl of 1 to 10 carbon atoms,

Xa is CH or N,

Ya is one or more substituent selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 10 carbon atoms, alkoxy of 1 to 10 carbon atoms, alkylthio of 1 to 10 carbon atoms, alkylamino of 1 to 10 carbon atoms, alkanol of 1 to 10 carbon atoms, aralkyl, aryl of 6 to 10 carbon atoms and 3 to 10 membered heterocycle;

n is an integer from 0 to 2,

J is a counter ion.

In still a further embodiment, $R_1$ and $R_2$ are independently optionally substituted lower alkyl of 1 to 10 carbon atoms;

Xa is CH;

Ya is one or more substituent selected from hydrogen, halogen, amino, amido, hydroxyl, alkyl of 1 to 6 carbon atoms, alkoxy of 1 to 6 carbon atoms and alkanol of 1 to 6 carbon atoms;

n is 1 or 2;

J is a halogen.

In another embodiment, the compounds for use in the method of the invention has the formula:

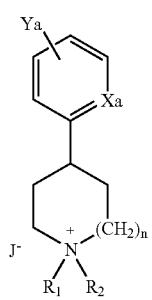

wherein $R_1$ and $R_2$ are independently optionally substituted lower alkyl of 1 to 6 carbon atoms;

Xa is CH;

Ya is one or more substituent selected from hydrogen, halogen, amino, amido, hydroxyl, alkyl of 1 to 6 carbon atoms, alkoxy of 1 to 6 carbon atoms, lower alkanol of 1 to 6 carbon atoms;

n is 1 or 2;

J is a halogen.

In an additional embodiment, $R_1$ and $R_2$ are independently selected from methyl, ethyl, n-propyl, or i-propyl;

Xa is CH;

Ya is hydrogen;

n is 1 or 2;

J is a halogen.

In an additional embodiment, the compound has the formula:

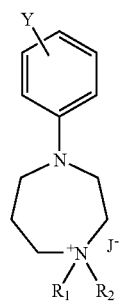

wherein $R_1$ and $R_2$ are independently selected from methyl, ethyl, n-propyl, or i-propyl;

Ya is hydrogen;

J is a halogen.

In a further embodiment, the compound for use in the method of the invention has the formula:

ASM-002

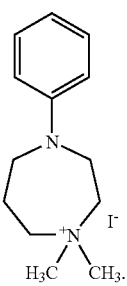

In a further embodiment, the compound for use in the method of the invention has the formula selected from:

ASM-003

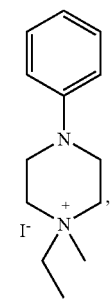

-continued

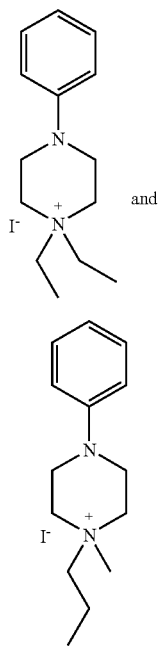

ASM-005 and

ASM-004

In still a further embodiment, the compound for use in the method of the invention has the formula selected from:

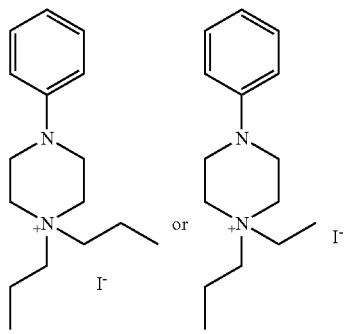

In one embodiment, the method according to the invention makes use of a compound that has the formula:

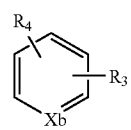

wherein $R_3$ is selected from

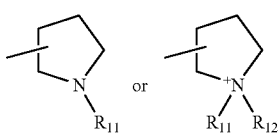

Xb is N or $N^+$—$R_{10}$,
$R_4$ is one or more substituent selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 10 carbon atoms, alkoxy of 1 to 10 carbon atoms, alkylthio of 1 to 10 carbon atoms, alkylamino of 1 to 10 carbon atoms, alkanol of 1 to 10 carbon atoms, aralkyl, aryl of 6 to 10 carbon atoms;

each of $R_{11}$ and $R_{12}$ are independently alkyl of 1 to 10 carbon atoms, provided that a counterion is present when Xb is $N^+$—$R_{10}$.

In one embodiment, $R_4$ is one or more substituent selected from hydrogen, halogen, amino, amido, hydroxyl, alkyl of 1 to 6 carbon atoms, alkoxy of 1 to 6 carbon atoms and alkanol of 1 to 6 carbon atoms; and $R_{11}$ and $R_{12}$ are independently alkyl of 1 to 6 carbon atoms.

In a further embodiment, $R_4$ is one or more substituent selected from hydrogen, and halogen; and $R_{11}$ and $R_{12}$ are independently alkyl of 1 to 6 carbon atoms.

In a further embodiment, the compound for use in the method of the invention has the formula selected from:

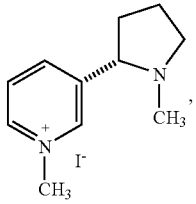

ASM-N1

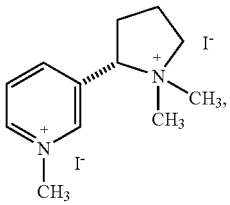

ASM-N2

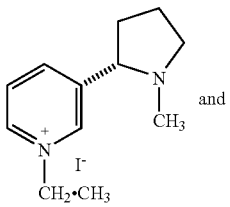

ASM-N3 and

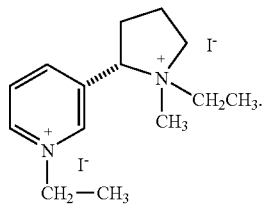

ASM-N4

In one embodiment, the method according to the invention makes use of a compound that has the formula:

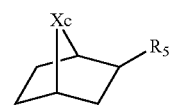

wherein Xc is $NR_{13}$ or $N^+$—$R_{13}R_{14}$, wherein $R_{13}$ and $R_{14}$ are independently alkyl of 1 to 10 carbon atoms $R_5$ is a 3 to 10 membered heterocycle,
provided that a counterion is present when Xc is $N^+$—$R_{13}R_{14}$.

In one embodiment, $R_{13}$ and $R_{14}$ are independently alkyl of 1 to 6 carbon atoms.

In another embodiment, $R_{13}$ and $R_{14}$ are independently alkyl of 1 to 6 carbon atoms; and $R_5$ is a 3 to 6 membered heterocycle.

In a further embodiment, $R_{13}$ and $R_{14}$ are independently alkyl of 1 to 6 carbon atoms; and $R_5$ is an optionally substituted pyridyl.

In a further embodiment, the for use in the method of the invention has the formula selected from:

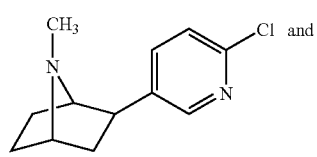

ASM-E1 and

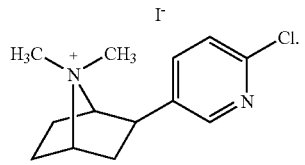

ASM-E2

In one embodiment, the method according to the invention makes use of a compound that has the formula:

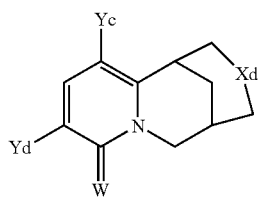

wherein W is O or S;
each of Yc and Yd are independently a substituent selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 10 carbon atoms, alkoxy of 1 to 10 carbon atoms, alkylthio of 1 to 10 carbon atoms, alkylamino of 1 to 10 carbon atoms, alkanol of 1 to 10 carbon atoms, aralkyl, aryl of 6 to 10 carbon atoms;
wherein Xd is $NR_{15}$ or $N^+$—$R_{15}R_{16}$, wherein $R_{15}$ and $R_{16}$ are independently alkyl of 1 to 10 carbon atoms,
provided that a counterion is present when Xd is $N^+$—$R_{15}R_{16}$.

In one embodiment, Yc and Yd are independently one or more substituent selected from hydrogen, halogen, amino, amido, hydroxyl, alkyl of 1 to 6 carbon atoms, alkoxy of 1 to 6 carbon atoms and alkanol of 1 to 6 carbon atoms.

In one embodiment, W is O; each of Yc and Yd are independently one or more substituent selected from hydrogen, halogen, amino, amido, hydroxyl, alkyl of 1 to 6 carbon atoms, alkoxy of 1 to 6 carbon atoms and alkanol of 1 to 6 carbon atoms;
and Xd is $NR_{15}$ or $N^+$—$R_{15}R_{16}$, wherein $R_{15}$ and $R_{16}$ are independently alkyl of 1 to 6 carbon atoms.

In a further embodiment, W is O; each of Yc and Yd are independently one or more substituent selected from hydrogen and halogen; and Xd is $NR_{15}$ or $N^+$—$R_{15}R_{16}$, wherein $R_{15}$ and $R_{16}$ are independently alkyl of 1 to 6 carbon atoms.

In a further embodiment, the compound for use in the method of the invention has the formula selected from:

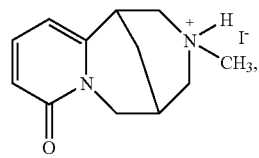

ASM-C1

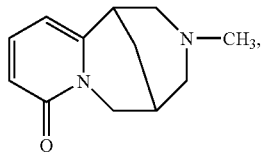

ASM-C2

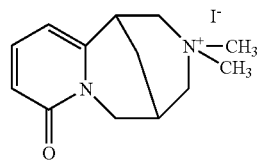

ASM-C3

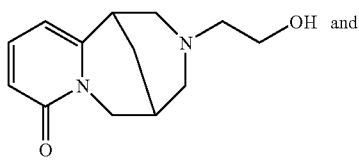

ASM-C4 and

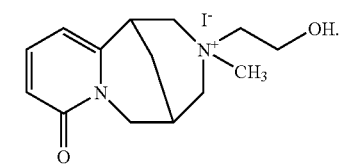

ASM-C5

In one embodiment, the pulmonary inflammatory disease is selected from the group consisting of asthma, chronic obstructive pulmonary disease (COPD), interstitial pulmonary fibrosis (IPF), sarcoidosis, hypersensitivity pneumonitis (HP), chronic HP and bronchiolitis obliterans with organizing pneumonitis (BOOP).

In one embodiment, the pulmonary inflammatory disease is selected from the group consisting of asthma, chronic obstructive pulmonary disease (COPD), interstitial pulmonary fibrosis (IPF), sarcoidosis, hypersensitivity pneumonitis (HP), and chronic HP.

In further embodiments, the pulmonary inflammatory disease is:
chronic obstructive pulmonary disease (COPD);
sarcoidosis;
hypersensitivity pneumonitis (HP).

In a further embodiment, the pulmonary inflammatory disease is asthma

In one embodiment of the invention, the compound for use in the method of the invention is administered orally, parenteraly, topically or by inhalation.

Alternatively, the compound is administered orally, topically, or by inhalation.

In one embodiment of the invention, the compound for use in the method of the invention is administered orally.

In one embodiment, the compounds described herein are useful for the manufacture of a medicament for treating pulmonary inflammatory diseases.

In one embodiment, there are novel compounds provided having the formula:

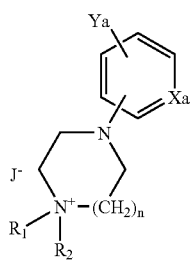

wherein $R_1$ and $R_2$ are independently lower alkyl of 1 to 10 carbon atoms,
Xa is CH or N,
Ya is one or more substituent selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 6 carbon atoms, alkoxy of 1 to 6 carbon atoms, alkylthio of 1 to 6 carbon atoms, alkylamino of 1 to 6 carbon atoms, alkanol of 1 to 6 carbon atoms, aralkyl, aryl of 6 to 10 carbon atoms and 3 to 10 membered heterocycle
n is an integer from 0 to 2,
J is a counter ion.
In a further embodiment $R_1$ and $R_2$ are independently optionally substituted alkyl of 1 to 6 carbon atoms;
Xa is CH;
Ya is one or more substituent selected from hydrogen, halogen, amino, amido, hydroxyl, alkyl of 1 to 6 carbon atoms, alkoxy of 1 to 6 carbon atoms and alkanol of 1 to 6 carbon atoms;
n is 1 or 2;
J is a halogen.
In one embodiment, the compound has the formula:

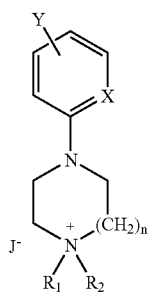

wherein $R_1$ and $R_2$ are independently optionally substituted alkyl of 1 to 6 carbon atoms;
X is CH;
Y is one or more substituent selected from hydrogen, halogen, amino, amido, hydroxyl, alkyl of 1 to 6 carbon atoms, alkoxy of 1 to 6 carbon atoms, alkanol of 1 to 6 carbon atoms;
n is 1 or 2;
J is a halogen.
In a further embodiment, $R_1$ and $R_2$ are independently selected from methyl, ethyl, n-propyl, or i-propyl;
X is CH;
Y is hydrogen;
n is 1 or 2;
J is a halogen.

In an alternative embodiment, the compound has the formula:

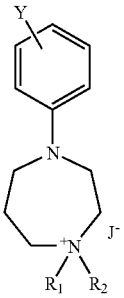

wherein $R_1$ and $R_2$ are independently selected from methyl, ethyl, n-propyl, or i-propyl;
Y is hydrogen;
J is a halogen.
In still a further embodiment, the compound has the formula:

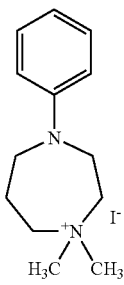

ASM-002

The first nicotinic receptor agonists include dimethylphenylpiperazinium (DMPP), nicotine, epibatidine, cytisine, acetylcholine and analogues thereof.

Alternatively, nicotinic receptor agonists that can be used for the treatments and uses according to the invention include the following nicotinic receptor agonists and analogues thereof:

1-DMPP and analogs thereof

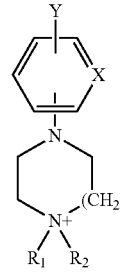

| Compound | $R_1$ | $R_2$ | X | Y | N |
|---|---|---|---|---|---|
| DMPP | $CH_3$ | $CH_3$ | CH | — | 1 |
|  | $CH_3$ | $CH_2CH_2CH_3$ | CH | — | 1 or 2 |
|  | $CH_2CH_3$ | $CH_2CH_3$ | CH | — | 1 or 2 |
|  | $CH_2CH_3$ | $CH_3$ | CH | — | 1 or 2 |
|  | $CH_3$ | $CH_3$ | CH | — | 2 |
|  | $CH_3$ | — | N | — | 1 |
|  | H | — | N | halogen | 1 |

2-Nicotine and analogs

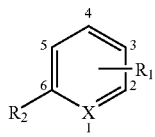

| Compd | X | R₁ | Position of R₁ | R₂ |
|---|---|---|---|---|
| Nicotine | N | (2-methylpyrrolidin-1-yl, N-CH₃) | 3 | H |
| | N | (2-ethylpyrrolidin-1-yl, N-CH₃) | 3 | H |
| | N | (isoxazole-vinyl group with 3-CH₃) | 3 | H |
| | N | (cyclopropyl-CH-Y) | 4 | H |
| | N | (pyrrolidinium with (CH₂)n, R₁, R₂) | 3 | Halogen |
| | N | (pyrrolidinium with (CH₂)n, R₁, R₂) | 3 | H |
| | N | (2-ethyl pyrrolidinium with (CH₂)n, R₁, R₂) | 3 | H |

3-Analogs of pyridylether

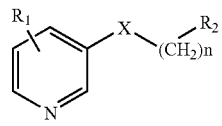

| Compd | X | R₁ | R₁ Position | R₂ | n |
|---|---|---|---|---|---|
| | O | H | — | (N-methylpyrrolidin-2-yl) | 1 |

3-Analogs of pyridylether

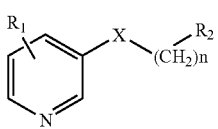

| Compd | X | R₁ | Position R₁ | R₂ | n |
|---|---|---|---|---|---|
| | O | Aryl, alkyl, substituted-phenyl | 5 | (N-methylpyrrolidin-2-yl) | 1 |
| | O | halogen | 6 | (2-methyl-NH bicyclic) | 1 |
| | O | H | — | (pyrrolidinium (CH₂)n with R₁, R₂) R1 and R2 = alkyl, n = 1 or 2 | 1, 2 or 3 |
| | NCH₃ | H | — | (pyrrolidinium (CH₂)n with R₁, R₂) R1 and R2 = alkyl, n = 1 or 2 | 1, 2 or 3 |

4-Epibatidine and analogs

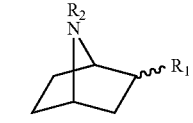

| Compound | R₁ | R₂ |
|---|---|---|
| Epibatidi-ne | (5-methylpyridin-2-yl, X = halogen) | H |
| | (3-phenyl-5-methylpyridin-2-yl, X = halogen) | H |
| | (3-methyl-5-methylisoxazol-... ) | H |

-continued

4-Epibatidine and analogs

| Compound | R₁ | R₂ |
|---|---|---|
| | 4-methylpyridazine | H |
| | 5-methyl-2-halopyridine (X = halogen) | H or CH₃(alkyl) |
| | pyrrolidinium (R1 and R2 = alkyl, n = 1 or 2) | H or CH₃(alkyl) |
| | 5-methyl-2-trimethylammoniumpyridine (X = N⁺(CH₃)₃) | H or CH₃(alkyl) |

5-Trimethaphan and analogs

| Compound | R | X |
|---|---|---|
| Trimethaphan | phenyl | — |
| | halophenyl | Halogen |
| | N⁺(CH₃)₃ | — |
| | N⁺(CH2CH₃)₃ | — |

6-Cytisine and analogs

| Compound | R | W | X | Y | Z |
|---|---|---|---|---|---|
| Cytisine | H | O | H | H | H |
| | nBu | O | H | H | H |
| | H | O | halogen | H | halogen |
| | H | S | H | H | H |
| | (CH₃)₂ | O or S | halogen | H | halogen |
| | (CH₂CH₃)CH₃ | O or S | H | H | H |
| | (CH₂CH₃)₂ | O or S | H | H | H |

7-Acetylcholine and analogs

| Compound | R |
|---|---|
| Acetylcholine | N⁺(CH₃)₃ |
| | N⁺(CH₂CH₃)₂CH₃ |
| | N⁺(CH₂CH₃)₃ |

8-N-methylcarbamylcholine and analogs

| Compound | R |
|---|---|
| N-methylcarbamylcoline | N⁺(CH₃)₃ |
| * | N⁺(CH₂CH₃)₂ CH₃ |
| * | N⁺(CH₂CH₃)₃ |

9-ABT-418 and analogs

| Compound | R |
|---|---|
| ABT-418 | CH₃ |
| | (CH₃)₂ |
| | (CH₂CH₃)CH₃ |
| | (CH₂CH₃)₂ |

10-GTS-21 and analogs

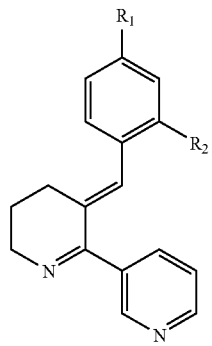

| Compound | $R_1$ | $R_2$ |
|---|---|---|
| GTS-21 | $OCH_3$ | $OCH_3$ |
|  | $N^+(CH_3)_3$ | $OCH_3$ |
|  | $OCH_3$ | $N^+(CH_3)_3$ |

11-Arecoline and analogs

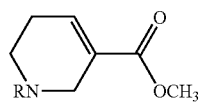

| Compound | R |
|---|---|
| Arecoline | $CH_3$ |
|  | $(CH_3)_2$ |
|  | $(CH_2CH_3)CH_3$ |
|  | $(CH_2CH_3)_2$ |

12-Lobeline and analogs

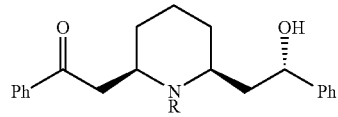

| Compound | R |
|---|---|
| Lobeline | H |
|  | $(CH_3)_2$ |
|  | $(CH_2CH_3)CH_3$ |
|  | $(CH_2CH_3)_2$ |

13-Analogs of philanthotoxin-433

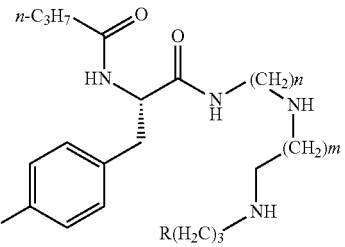

| Compound | R | n | m |
|---|---|---|---|
|  | $NH_2$ | 4 | 3 |
|  | $N^+(CH_3)_3$ | 1, 2, 3 or 4 | 1, 2 or 3 |
|  | $N^+(CH_2CH_3)_2CH_3$ | 1, 2, 3 or 4 | 1, 2 or 3 |
|  | $N^+(CH_2CH_3)_3$ | 1, 2, 3 or 4 | 1, 2 or 3 |

14- Azabicyclic analogs

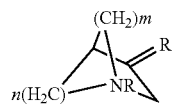

| Compound | R | R | n | m |
|---|---|---|---|---|
| 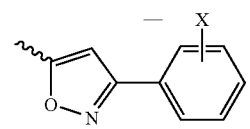 |  | — | 2 | 2 |
| Het |  | — | 2 | 2 |
| (acyl) |  | — | 2 | 2 |
| (isoxazole-phenyl) | — | X | 2 | 2 |
| (dimethylisoxazole) | $CH_3$ | $CH_3$ | 1 or 2 | 1 or 2 |
| (methylisoxazole-phenyl) | $CH_3$ | X | 1 or 2 | 1 or 2 |

15-Analogs of SIB-1553

| Compound | R | n |
|---|---|---|
|  | $CH_3$ | 1 (threo) |
|  | $CH_3$ | 0 (erythro) |
|  | $CH_3$ | 0 (threo) |
|  | $(CH_3)_2$ | 0 or 1 |
|  | $(CH_2CH_3)CH_3$ | 0 or 1 |
|  | $(CH_2CH_3)_2$ | 0 or 1 |

16-Analogs of imidacloprit

| Compound | R | X | Y | Z |
|---|---|---|---|---|
|  | $NO_2$ | Cl | H | NH |
|  | H | Cl | $N_3$ | S |
|  | $NO_2$ | Cl | $N_3$ | S |
|  | $N^+(CH_3)_3$ | Cl | H | NH |
|  | $NO_2$ | $N^+(CH_3)_3$ | H | NH |
|  | $NO_2$ | Cl | $N^+(CH_3)_3$ | NH |

Of particular interest for the treatment of inflammatory pulmonary diseases are the following analogues of DMPP, and having the formula:

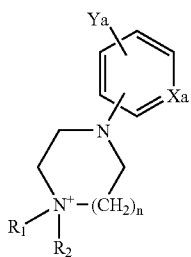

in which $R_1$ is methyl or ethyl, $R_2$ is methyl, ethyl or propyl, X is CH, Y is hydrogen, n is 1 or 2.

The term "lower alkyl" represents a linear, branched or cyclic hydrocarbon moiety having 1 to 10 carbon atoms and preferably 1 to 6 carbon atoms, which may have one or more unsaturation in the chain, and is optionally substituted. Examples include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl, butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cyclohexenyl, cyclohex-dienyl and cyclohexyl. The term "lower alkyl" is also meant to include alkyls in which one or more hydrogen atom is replaced by a halogen, ie. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl.

The term "lower alkoxy" represents an alkyl which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy.

The term "lower Alkylthio" represents an alkyl which is covalently bonded to the adjacent atom through a sulfur atom Examples include but are not limited to methylthio, ethylthio, propylthio, isopropylthio, butylthio, isobutylthio, sec-butylthio and tert-butylthio.

The term "lower Alkylamino" represents an alkyl which is covalently bonded to the adjacent atom through a nitrogen atom and may be monoalkylamino or dialkylamino, wherein the alkyl groups may be the same or different. Examples include but are not limited to methylamino, dimethylamino, ethylamino, diethylamino, methylethylamino, propylamino, isopropylamino, butylamino, isobutylamino, sec-butylamino, tert-butylamino, pentylamino, isopentylamino, neopentylamino, tert-pentylamino, hexylamino, isohexylamino and neohexylamino, The term "lower alkanol" represents an "alkyl" moiety for which one of the hydrogens has been replaced by an hydroxyl group. The term alkanol is also meant to include alkanol in which one or more hydrogen atoms is replaced by a halogen. Examples include but are not limited to methanol, ethanol, propanol, isopropanol, butanol, ethyleneglycol, propyleneglycol, cyclopropanol or trifluoroethanol or fluoromethanol.

The term "aralkyl" represents an aryl group attached to the adjacent atom by a $C_{1-6}$ alkyl Examples include but are not limited to benzyl, benzhydryl, trityl, phenethyl, 3-phenylpropyl, 2-phenylpropyl, 4-phenylbutyl and naphthylmethyl.

The term "aryl" represents a carbocyclic moiety containing at least one benzenoid-type ring (i.e. may be monocyclic or polycyclic) having 6 to 10 carbon atoms, and which may be optionally substituted with one or more substituents. Alternatively, the ring may be containing 6 carbon atoms. Examples include but is not limited to phenyl, tolyl, dimethyphenyl, aminophenyl, anilinyl, naphthyl, anthryl, phenanthryl or biphenyl, The term "Acyl" is defined as a radical derived from a carboxylic acid, obtained by replacement of the —OH group. Like the acid to which it is related, an acyl radical may be straight chain, branched chain or cyclic aliphatic or aromatic. Examples include but are not limited to formyl, acetyl, propionyl, butyryl, isobutyryl, valeryl, isovaleryl, pivaloyl, caproyl, isocaproyl, acryloyl, propioloyl, methacryloyl, crotonoyl, isocrotonoyl, benzoyl, naphthoyl, toluoyl, cinnamoyl, furoyl, glyceroyl, salicyloyl.

The term "Acyloxy" represents an acyl which is covalently bonded to the adjacent atom through an oxygen atom. Examples include but are not limited to formyloxy, acetyloxy, propionyloxy, butyryloxy, isobutyryloxy, valeryloxy, isovaleryloxy, pivaloyloxy, caproyloxy, isocaproyloxy, acryloyloxy, propioloyloxy, methacryloyloxy, crotonoyloxy, isocrotonoyloxy, benzoyloxy, naphthoyloxy, toluoyloxy, hydroatropoyloxy, atropoyloxy, cinnamoyloxy, furoyloxy, glyceroyloxy, tropoyloxy, benziloyloxy, salicyloyloxy, anisoyloxy, vanilloyloxy, veratroyloxy, piperonyloyloxy, protocatechuoyloxy and galloyloxy, with preference given to formyloxy, acetyloxy, propionyloxy, butyryloxy, isobutyryloxy, valeryloxy, isovaleryloxy, pivaloyloxy, benzoyloxy and naphthoyloxy.

The term "halogen atom" is specifically a fluoride atom, chloride atom, bromide atom or iodide atom.

The term "counterion" is meant to include ion that accompanies an ionic species in order to maintain electric neutrality. Examples of counterion as used herein include but are not limited to fluoride, chloride, bromide, iodide, sulfate, sulfonate.

The term "independently" means that a substituent can be the same or a different definition for each item.

The term "heterocycle" represents a 3 to 10 membered optionally substituted saturated, unsaturated or aromatic cyclic moiety wherein said cyclic moeity is interrupted by at least one heteroatom selected from oxygen (O), sulfur (S) or nitrogen (N). Alternatively, heterocycles may be 3 to 6 membered ring or 5 to 6 membered ring. Heterocycles may be monocyclic or polycyclic rings. Examples include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl; morpholinyl, morpholino, oxetanyl, oxadiazolyl, oxiranyl, oxazinyl oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl and thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

For the purposes of the present application, the term "animal" is meant to signify human beings, primates, domestic animals (such as horses, cows, pigs, goats, sheep, cats, dogs, guinea pigs, mice, etc.) and other mammals. Generally, this term is used to indicate living creatures having highly developed vascular systems.

For the purposes of the present invention, agonists or agents or ligands are molecules or compounds that bind to and modulate the function of the nicotinic receptor. Preferred agents are receptor-specific and do not cross the blood-brain barrier, such as DMPP. Useful agents may be found within numerous chemical classes, though typically they are organic compounds and preferably, small organic compounds. Small organic compounds have a molecular weight of more than 150 yet less than about 4,500, preferably less than about 1500, more preferably, less than about 500. Exemplary classes include peptides, saccharides, steroids, heterocyclics, polycyclics, substituted aromatic compounds, and the like.

Nicotinic agonists would not necessarily replace all drugs that are currently used to specifically treat inflammatory lung diseases and the airflow obstruction that is often associated with these diseases. Bronchodilators remain useful for the immediate release of bronchospasms. However, bronchodilators have no effect on the underlying cause of inflammation.

Nicotinic agonists may be useful as a steroid sparing or replacing drug. By targeting their delivery to the lung phagocytes, these drugs could be helpful in controlling both airway and interstitial inflammation. One major advantage of nicotinic agonists over corticosteroids, besides being expected to have fewer side effects, is the fact that these agonists may have a direct effect on fibroblasts and could therefore prevent or reverse fibrosis in the airways and in the lungs, something corticosteroids cannot do. Interstitial fibrosis is the hallmark if IPF, a major sequel of HP and sarcoidosis, and airway fibrosis is a prevailing finding in chronic asthma (57).

Other substances are actively being studied as potential new treatments for inflammatory lung diseases. Many cytokines are specifically targeted (e.g. IL-5, IL-13, IL-16 and the like) (62). It is believed that because of the complexity of pathways involved in inflammation, any one specific cytokine or other inflammatory mediator is unlikely to have a significant impact on the treatment of these lung diseases. Nicotinic receptor agonists as well as analogs and derivatives thereof, not unlike corticosteroids, have the advantage of targeting a broad spectrum of the inflammatory response. Therein lies their potential in the treatment of inflammatory lung diseases.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways as described above, e.g. to enhance their proteolytic stability. Other methods of stabilization may include encapsulation, for example, in liposomes, etc. The subject binding agents are prepared in any convenient way known to those skilled in the art.

For therapeutic uses, agents affecting nicotinic receptor function may be administered by any convenient means. Small organics are preferably administered orally; other compositions and agents are preferably administered parenterally, conveniently in a pharmaceutically or physiologically acceptable carrier, e.g., phosphate buffered saline, or the like. Typically, the compositions are added to a retained physiological fluid such as blood or synovial In accordance with the invention, there is provided another embodiment which is a pharmaceutical composition for treating pulmonary inflammatory diseases comprising a nicotinic receptor agonist and a pharmaceutically acceptable excipient.

The carrier(s) or excipient(s) must be "acceptable" in the sense of being compatible with the other ingredients of the formulation and not being deleterious to the recipient thereof.

In an alternative embodiment, there is provided a pharmaceutical composition for treating pulmonary inflammatory diseases comprising
i) a compound of formula:

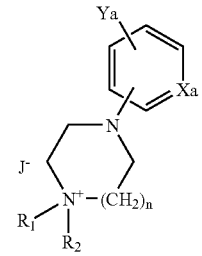

wherein $R_1$ and $R_2$ are independently lower alkyl of 1 to 10 carbon atoms,
Xa is CH or N,
Ya is one or more optional substituent selected from halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 6 carbon atoms, alkoxy of 1 to 6 carbon atoms, alkylthio of 1 to 6 carbon atoms, alkylamino of 1 to 6 carbon atoms, alkanol of 1 to 6 carbon atoms, aralkyl, aryl of 6 to 10 carbon atoms and 3 to 10 membered heterocycle n is an integer from 0 to 2, J is a counter ion;

or ii) a compound having the formula:

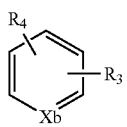

wherein $R_3$ is selected from

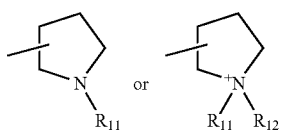

$Xb$ is $N$ or $N^+$—$R_{10}$, $R_4$ is one or more substituent selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 10 carbon atoms, alkoxy of 1 to 10 carbon atoms, alkylthio of 1 to 10 carbon atoms, alkylamino of 1 to 10 carbon atoms, alkanol of 1 to 10 carbon atoms, aralkyl, aryl of 6 to 10 carbon atoms;

each of $R_{10}$, $R_{11}$ and $R_{12}$ are independently alkyl of 1 to 10 carbon atoms, provided that a counterion is present when $Xb$ is $N^+$—$R_{10}$;

or iii) a compound having the formula:

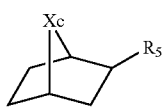

wherein $Xc$ is $NR_{13}$ or $N^+$—$R_{13}R_{14}$, wherein $R_{13}$ and $R_{14}$ are independently alkyl of 1 to 10 carbon atoms $R_5$ is a 3 to 10 membered heterocycle, provided that a counterion is present when $Xc$ is $N^+$—$R_{13}R_{14}$;

or iv) a compound having the formula:

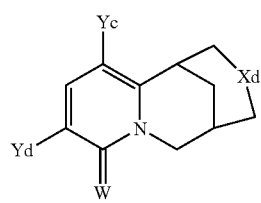

wherein W is O or S;

each of Yc and Yd are independently a substituent selected from hydrogen, halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 10 carbon atoms, alkoxy of 1 to 10 carbon atoms, alkylthio of 1 to 10 carbon atoms, alkylamino of 1 to 10 carbon atoms, alkanol of 1 to 10 carbon atoms, aralkyl, aryl of 6 to 10 carbon atoms;

wherein $Xd$ is $NR_{15}$ or $N^+$—$R_{15}R_{16}$, wherein $R_{15}$ and $R_{16}$ are independently alkyl of 1 to 10 carbon atoms;

provided that a counterion is present when $Xd$ is $N^+$—$R_{15}R_{16}$;

and a pharmaceutically acceptable excipient.

In one embodiment, the pharmaceutical composition as defined herein may be further comprising one or more therapeutic agent selected from a' bronchodilating agent, an anti-inflammatory agent, a leukotriene receptor antagonist or a phosdiesterase inhibitor (PDE) such as PDE IV.

In a further embodiment, the bronchodilating agent is β2 agonists or anticholinergics.

In a further embodiment, the an anti-inflammatory agent is corticosteroids.

In a further embodiment, the PDE inhibitor is PDE IV.

In another embodiment, the present invention provides a combination comprising a therapeutically effective amount of a compound useful in the method of the present invention, and a therapeutically effective amount of at least one or more therapeutic agent.

It will be clear to a person of ordinary skill that if a further additional therapeutic agent is required or desired, ratios will be readily adjusted. It will be understood that the scope of combinations described herein is not limited to the therapeutic agents listed herein, but includes in principles any therapeutic agent useful for the prevention and treatment of pulmonary inflammatory diseases.

For peptide agents, the concentration will generally be in the range of about 50 to 500 μg/ml. Alternatively, it may administered in an acceptable range of from about 1 mg to a few 10 g or more per Kg in a body weight basis) in the dose administered. Other additives may be included, such as stabilizers, bactericides; etc. These additives will be present in conventional amounts.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. Generally, the amount administered will be empirically determined, typically in the range of about 10 μg to 1000 mg/kg of the recipient or 10 μg to 100 mg/kg or 10 μg to 1 mg/kg for example.

The desired dose may conveniently be presented in a single dose or as divided dose administered at appropriate intervals, for example as two, three, four or more doses per day.

While it is possible that, for use in therapy, a compound or combination of the invention may be administered as the raw chemical it is preferable to present the active ingredient as a pharmaceutical composition.

As examples, many such therapeutics are amenable to direct injection or infusion, topical, intratracheal/nasal administration e.g. through aerosol, intraocularly, or within/on implants (such as collagen, osmotic pumps, grafts comprising appropriately transformed cells, etc. with therapeutic peptides.

Pharmaceutical compositions also include those suitable for oral, nasal, topical (including buccal and sub-lingual), transdermal, or parenteral (including intramuscular, sub-cutaneous and intravenous) administration or in a form suitable for administration by inhalation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Compositions suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

For administration by inhalation the compounds and combinations according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation, the compounds and combinations according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

Two animal models were used to study the effects of nicotinic antagonists in inflammatory pulmonary diseases: an HP model and an asthma model. With both of these models, the effects of nicotinic receptor agonists (both selective and non-selective) were studied on lung physiology, and inflammation. In vitro studies were performed using isolated inflammatory cells from the animal studies or from patients as well as commercially available cell lines in an attempt to understand the mechanisms by which nicotinic agonists down-regulate inflammation.

Initially, experiments were conducted with non-specific agonists, i.e agonists that bind to all nicotinic receptor sub-units (nicotine, dimethylphenylpiperazinium (DMPP) and epibatidine) (13, 42). A β4 subunit specific agonist, cytisine (42), was also tested to see whether a specific stimulation could also have anti-inflammatory effects.

Example I

In Vivo HP Studies—I—Hypersensitivity-Like Inflammation.

Effect of nicotinic agonists on long term-induced hypersensitivity pneumonitis (HP) in mice.

It is shown that the stimulation of nicotinic receptors with nicotine down-regulates the immune response to HP antigens via inflammatory cytokine suppression and inhibition of specific antigen-mediated cellular activation.

Figure 2:
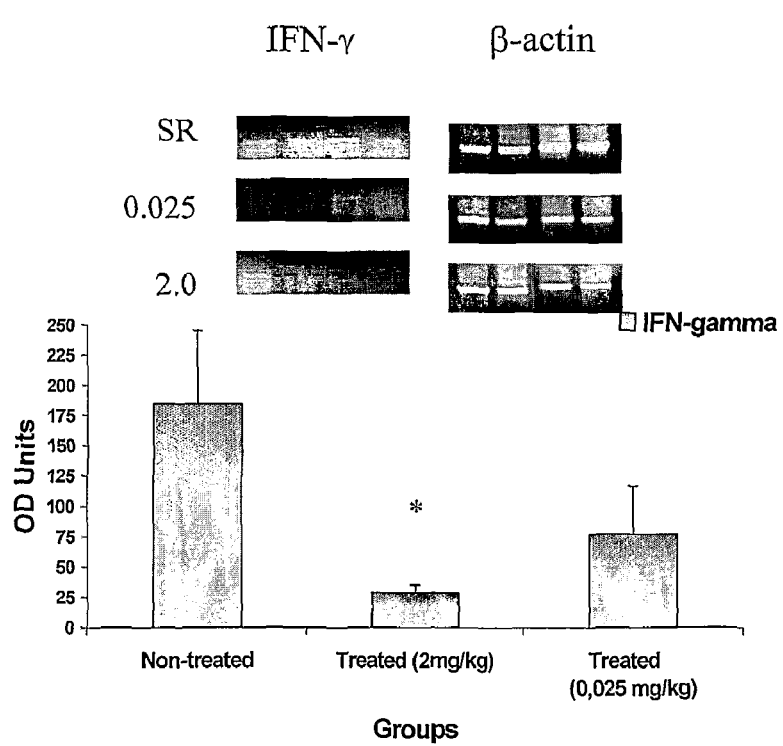
FIG. 2 shows IFN-γ mRNA expression in isolated lung mononuclear cells.

This model was selected because, as mentioned previously, the incidence of HP is lower in smokers than in non-smokers (50), and because this model is well described. HP was induced by the administration of *Saccharopolyspora rectivirgula* (SR) antigen, the causative agent of farmer's lung (51), a form of HP. Mice were simultaneously treated with intraperitoneal (IP) nicotine, with doses ranging from 0.5 to 2.0 mg/kg, twice a day. Nicotine administration significantly reduced the number of total cells found in the bronchoalveolar lavage (BAL) of these mice. The population that was the most affected by nicotine treatment were lymphocytes as seen in FIG. 1. It will be seen that there was a marked inhibition of total cell counts in nicotine treated mice due mainly to a decrease in the lymphocyte population. Pulmonary macrophages and lymphocytes were isolated, and stimulated with anti-CD3+ recombinant IL-2. The production of IFN-γ mRNA by these cells, a cytokine known to be involved in the development of HP and other pulmonary inflammatory diseases (52), was measured. Cells from nicotine treated animals showed significantly lower expression of IFN-γ mRNA than cells from non-treated animals. FIG. 2 illustrates that a significant inhibition of IFN-γ mRNA was observed.

Example II

In Vitro Studies Showing the Effect of Nicotinic Agonists on Cytokine Expression.

To further clarify the mechanisms involved in suppressive effect of nicotine in the in vivo model, an alveolar macrophage cell line was used.

Figure 3:
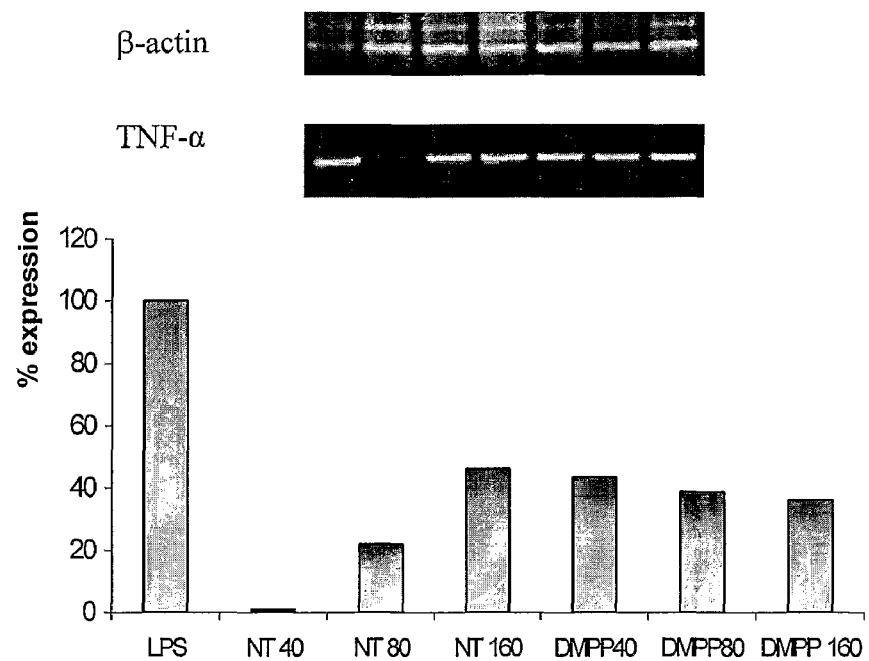
FIG. 3 illustrates TNF-α mRNA expression induced by a 24 h LPS stimulation.
Figure 4:
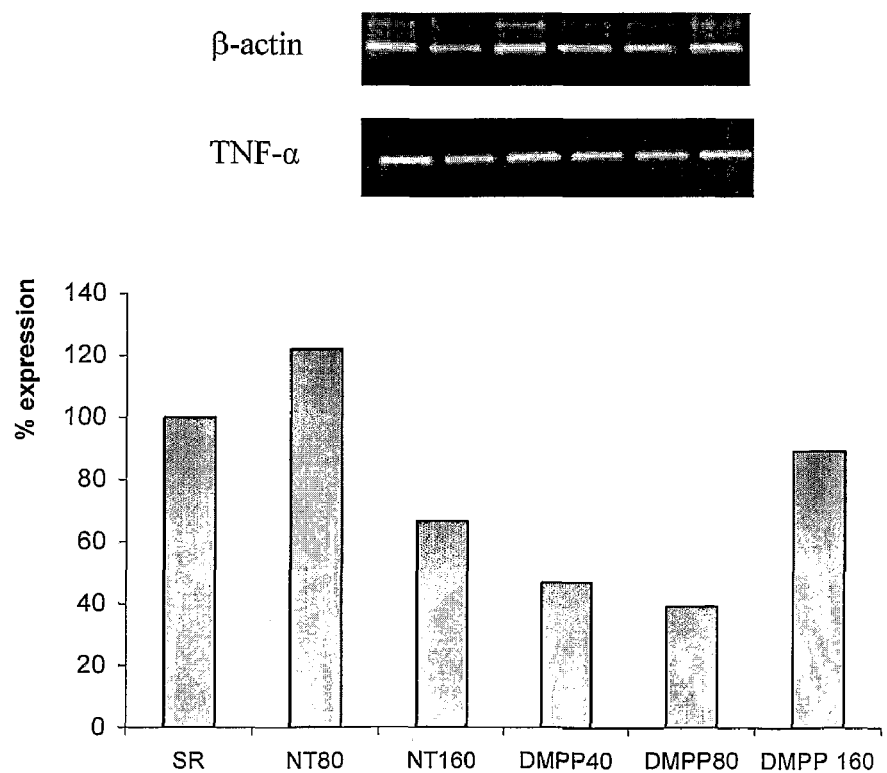
FIG. 4 illustrates TNF-α mRNA expression induced by a 24 h SR stimulation.
Figure 5:
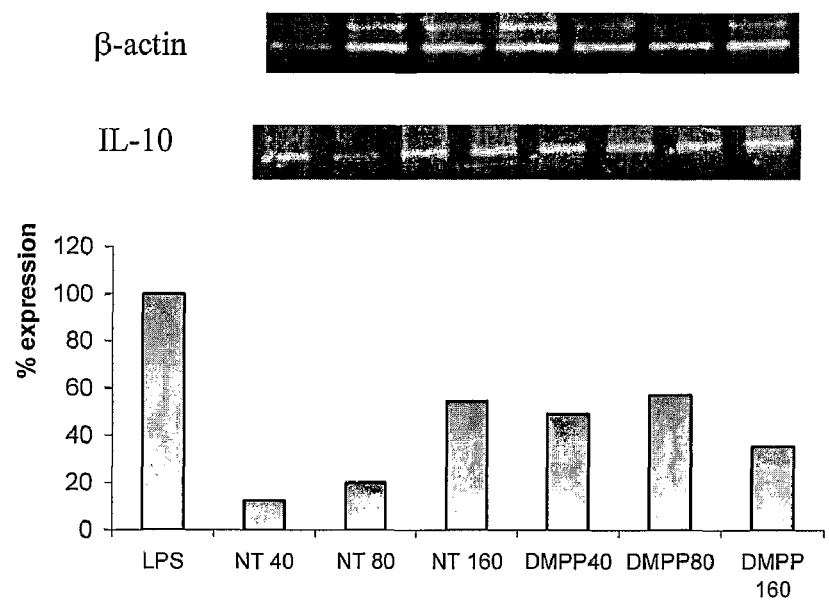
FIG. 5 illustrates IL-10 mRNA expression induced by a 24 h LPS stimulation.
Figure 6:
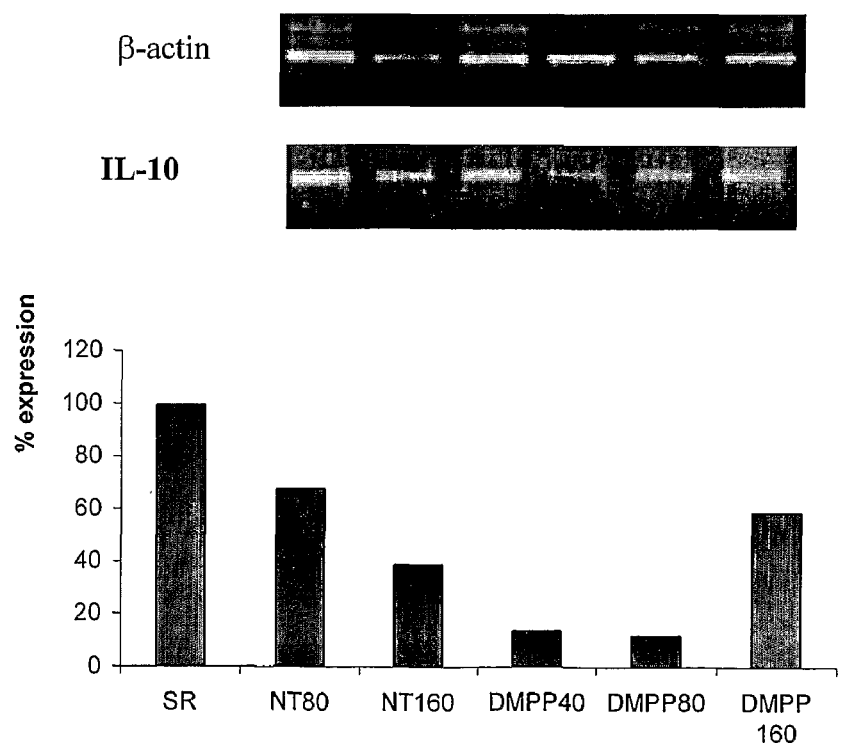
FIG. 6 illustrates IL-10 mRNA expression induced by a 24 h SR stimulation. nicotine treatment occurred at 160 μM (60% drop of expression), and at 80 μM (90% drop of expression) with the DMPP treatment.

The effect of nicotine or DMPP treatment on AMJ2-C11 cells was tested on TNF-α, IL-10 mRNA expression by RT-PCR. These cytokines are involved in the development of pulmonary inflammatory diseases such as HP, asthma and sarcoidosis (52-55). Nicotine and DMPP treatments showed a great decrease in TNF mRNA expression (up to a 98% reduction of expression in LPS stimulated cells treated with 40 μM nicotine), but not in a dose-dependent manner. Reference is made to FIG. 3 where results are expressed as a % of expression, 100% being attributed to the LPS alone group. The intensity of the band was obtained by dividing the intensity of the TNF-α band by that of β-actin. Treatment of stimulated cells with different doses (40 to 160 μM for nicotine and DMPP) induced a drop of TNF-α mRNA expression. The greatest effect was obtained with the 40 μM concentration of nicotine (a 98% reduction of expression), while all doses of DMPP caused a 60 to 50% reduction of expression. Similar results were observed with SR-stimulated cells. Reference is made to FIG. 4 where results are expressed as described in FIG. 5. Treatment of stimulated cells with different doses (80 and 160 μM for nicotine and 40 to 160 μM for DMPP) induced a down-regulation of TNF-α mRNA expression. Only the 160 μM dose of nicotine had an effect on mRNA expression, while the 40 and 80 μM doses of DMPP induced up to 60% of reduction of TNF-α mRNA expression. This non-dose dependent response can be explained by nicotinic receptor desensitization due to a large quantity of agonist in the medium. IL-10 mRNA expression was also reduced by nicotine and DMPP treatment. The maximal down-regulation occurred at a dosage of 40 μM nicotine (LPS stimulated; 88% reduction of mRNA expression; reference is made to FIG. 5 where results are expressed. Treatment of stimulated cells with different doses (40 to 160 μM for both nicotine and DMPP) induced a down-regulation of IL-10 mRNA expression. The largest drop of expression (a 87% reduction) occurred with 40 μM nicotine. DMPP induced a 55 to 40% reduction of expression for all three doses. At a dosage of 80 μM DMPP a 87% IL-10 mRNA expression reduction is observed in SR-stimulated cells, the results are given in FIG. 6. Treatment of SR-stimulated cells with different doses (80 and 160 μM for nicotine and 40 to 80 μM for DMPP) induced a down-regulation of IL-10 mRNA expression. The greatest drop in mRNA expression with the nicotine treatment occurred at 160 μM (60% drop of expression), and at 80 μM (90% drop of expression) with the DMPP treatment.

Figure 7:
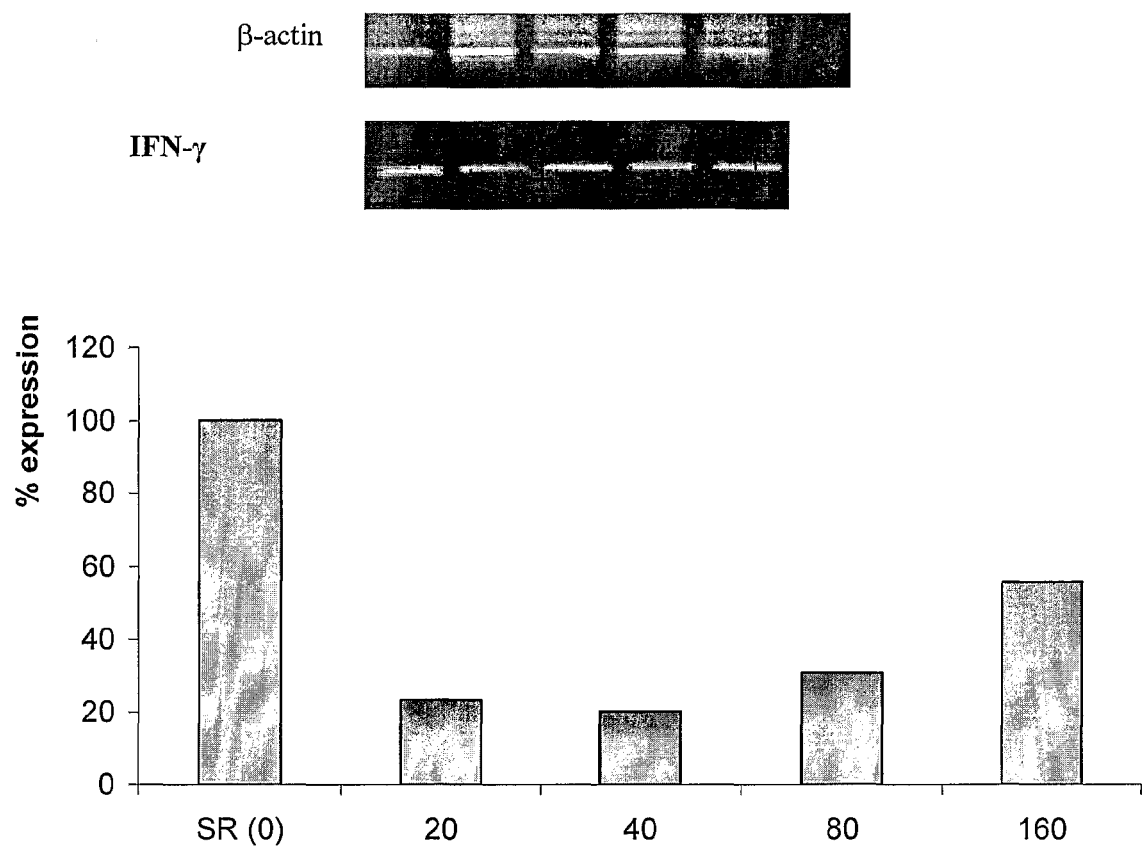
FIG. 7 illustrates IFN-γ mRNA expression induced in RAW 264.7 cells by a 24 h LPS stimulation.

Another macrophage cell line (RAW 264.7, ATCC) was used to test the effect of DMPP on IFN-γ expression by RT-PCR, because AMJ2-C11 cells did not appear to express IFN-γ mRNA (data not shown). Cells were stimulated with 50 μg/ml of SR antigen and incubated with DMPP at doses ranging from 40 to 160 μM. DMPP treatment reduced the expression of INF-γ in these cells by up to 75% with the 40 μM dose. Reference is made to FIG. 7 where results are expressed as described in FIG. 5. Treatment of stimulated cells with different doses of DMPP induced a reduction in IFN-γ mRNA expression. The largest drop of expression (a 80% reduction) occurred with 40 μM DMPP.

Example III

In Vitro Effects of Nicotinic Agonists on Co-Stimulatory Molecule Expression

Figure 8A:
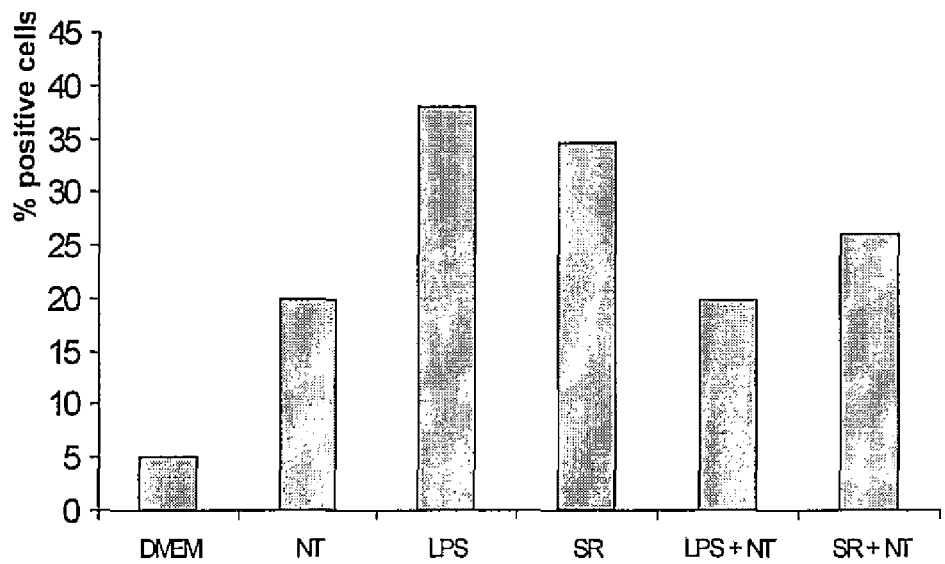
FIGS. 8 (a) and (b) show the expression of CD 80 induced with either LPS (38%) or SR antigen (35%)
Figure 8B:
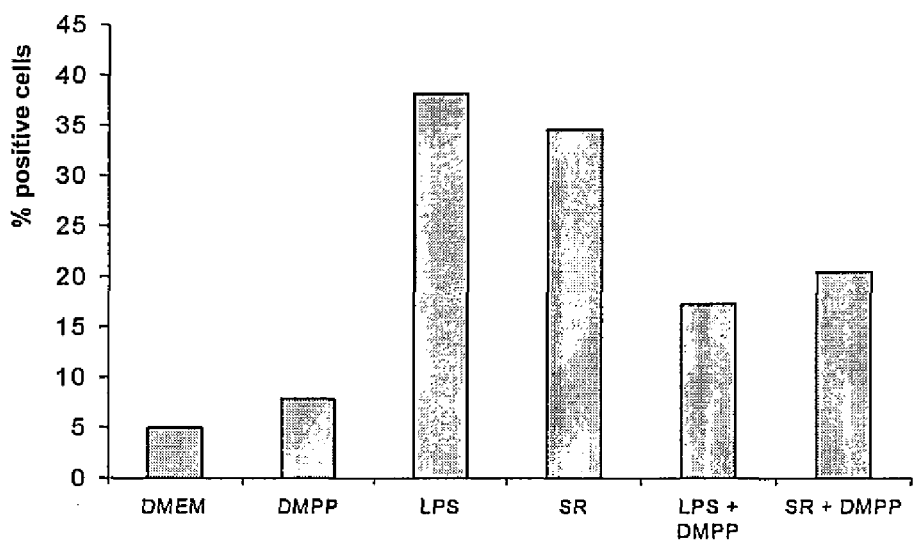

The effects of nicotine and DMPP on B7 (CD80) molecule expression were tested in vitro. AMJ2-C11 cells (mouse alveolar macrophages, from the ATCC) were incubated with 40 μM nicotine or DMPP and stimulated with LPS (0.1 μg/ml) or SR antigen (50 μg/ml) for 48 hours. The percentage of expression of CD80 in treated cells was about one half of the expression found in LPS and SR stimulated non-treated cells. Reference is made to FIG. 8 (*a*) which shows that nicotine treatment (40 μM for 48 h) reduced the expression to 20% in LPS stimulated cells. Reference is also made to FIG. 8 (*b*) which shows that DMPP treatment (40 μM for 48 h) reduced the expression to 17% in LPS stimulated cells and 20% in SR stimulated cells.

Example IV

Studies on Human BAL Cells (AM and Lymphocytes)

Figure 9:
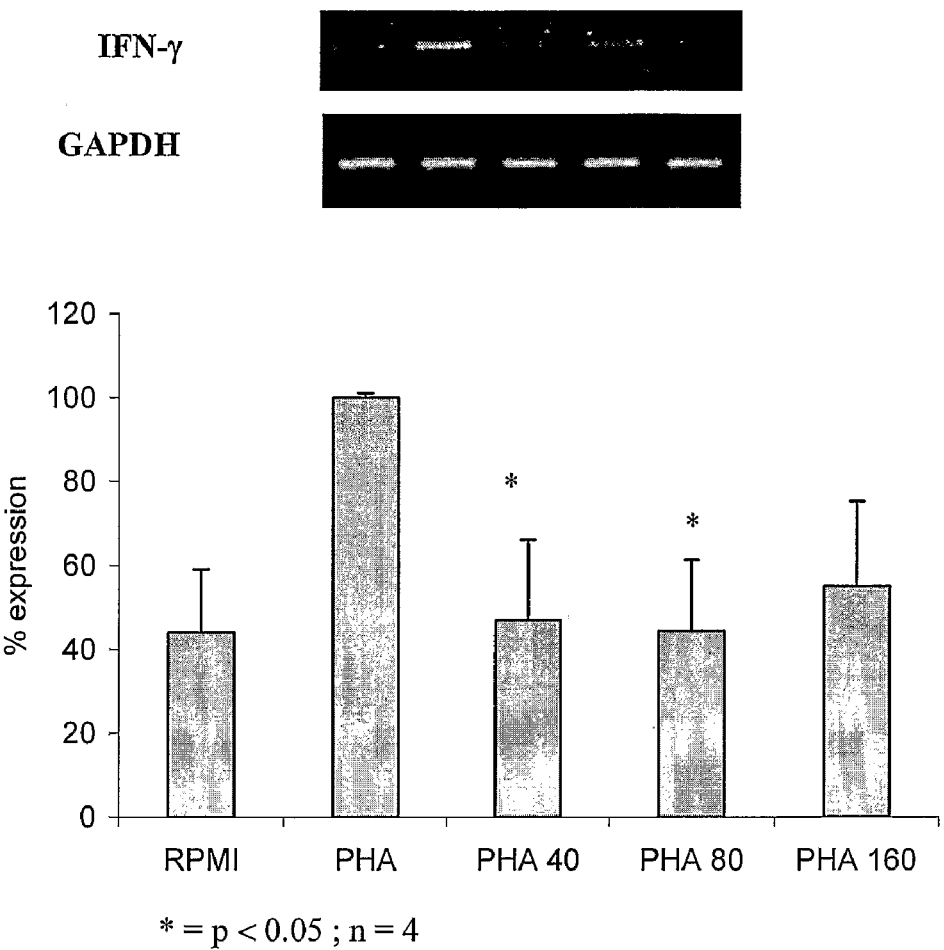
FIG. 9 illustrates IFN-γ mRNA expression in T lymphocytes isolated from BAL performed on HP patients.

Since one goal was to treat patients with DMPP or similar drugs, the effect of this drug was verified on lymphocytes from patients with HP. BAL were performed on patients with HP. Lymphocytes were isolated from the other BAL cells, stimulated with PHA and incubated with DMPP. The dose-response of DMPP were tested on cytokine mRNA production (by RT-PCR) for IFN-γ. Reference is made to FIG. 9 which shows that DMPP treatment reduced expression of IFN-γ in these cells.

Figure 10:
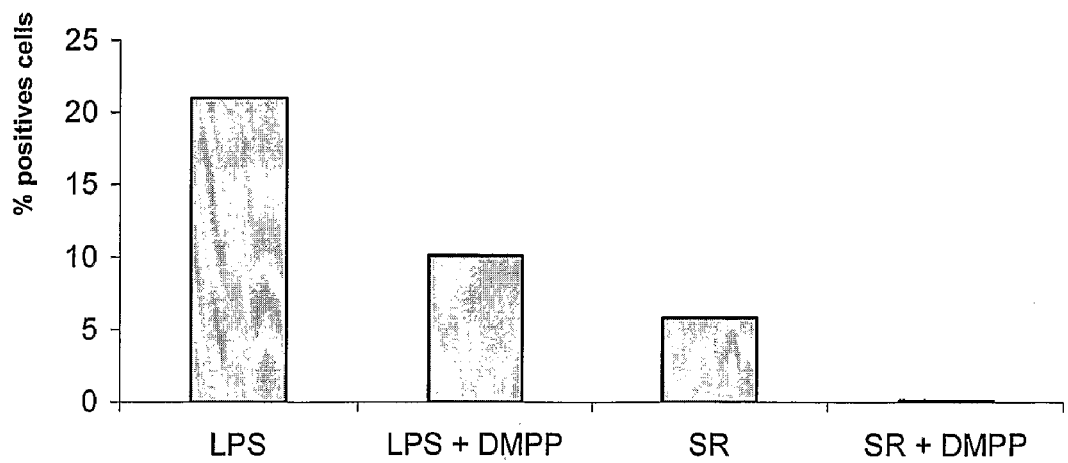
FIG. 10 illustrates CD 86 expression in total cells from a BAL that was performed on a normal patient.

A broncho-alveolar lavage was performed on a normal patient, and alveolar macrophages were isolated. SR-stimulated and nicotine or DMPP treated cells showed once again about half of the expression of CD86 than non-treated cells. Reference is made to FIG. 10 which shows that cells that were treated with DMPP express 50% less CD86 than non-treated cells.

Example V

Figure 11:
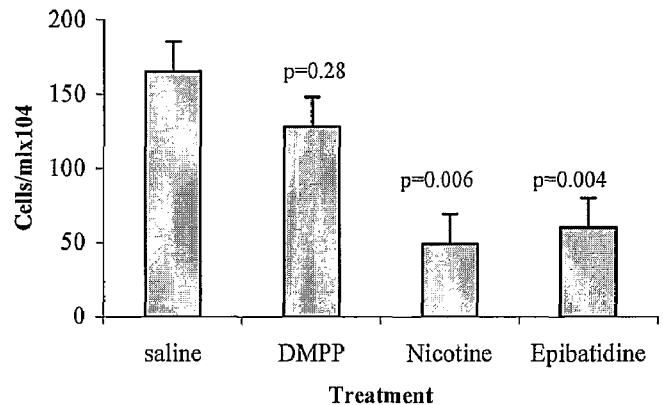
FIG. 11 illustrates BAL cells from DMPP, nicotine and epibatidine treated mice.

Investigation of the Effect of Other Nicotinic Agonists on the Short Term SR-Induced Acute Inflammation The intranasal instillation of *Saccharopolyspora rectivirgula* (SR) antigens, the causative agent for farmer's lung, to mice, induces a prominent inflammatory response in the lung. Neutrophils are the first inflammatory cells recruited at the site of inflammation. Treatment of mice with DMPP (0.5 mg/kg), nicotine (0.5 mg/kg) and epibatidine (2 μg/kg) had a marked inhibitory effect on SR-induced inflammation. Reference is made to FIG. 11 which shows that treatment with nicotine and epibatidine had a significant inhibitory effect on SR-induced inflammation after 24 hours. Nicotinic agonists were administered intra-nasally in 50 μl volume every 6 h and mice were sacrificed 24 hr after SR instillation.

Figure 12:
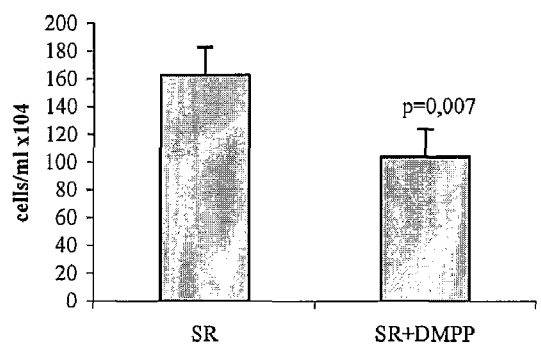
FIG. 12 illustrates a significant inhibitory effect of DMPP on lung inflammation was found when increasing the number of animals.

A significant inhibitory effect was observed with nicotine and epibatidine but not with DMPP. However, after increasing the number of mice treated or not treated with DMPP to 15, we did observe a significant inhibition compared to the non-treated group (FIG. 12).

Figure 13:
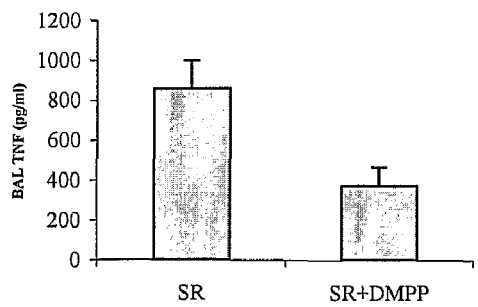
FIG. 13 illustrates TNF levels in BAL fluid from DMPP-treated mice.

Levels of TNF (a pro-inflammatory cytokine) are lower in the broncho-alveolar lavage of DMPP-treated mice (FIG. 13 shows that DMPP decreased significantly BALF TNF levels) indicating that the down-regulation of inflammation may result from lower TNF concentrations.

Example VI

In Vivo Asthma Model.

Similar experiments were performed in ovalbumin-sensitized mice. DMPP allegedly decreases both the inflammatory response and the hyper-responsiveness to inhaled allergens and methacholine.

Groups of Balb/c mice were sensitized by intra-peritoneal injection of 20 μg

Figure 14:
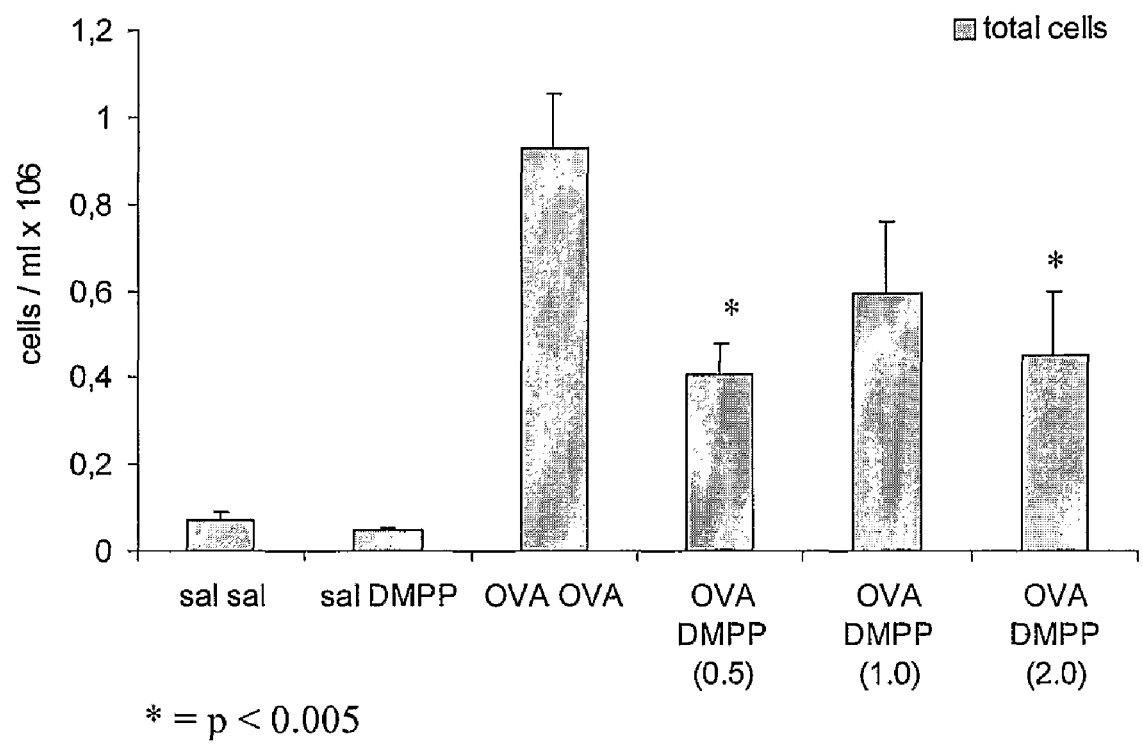
FIG. 14 illustrates the effect of intra-peritoneal treatment with increasing doses of DMPP on total cell accumulation in BAL of asthmatic mice.
Figure 15:
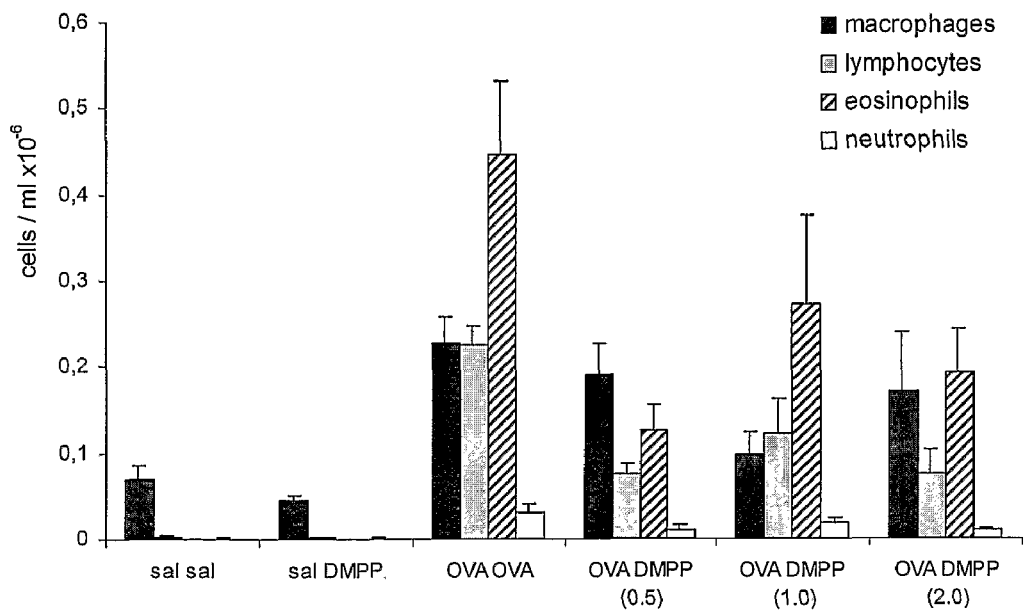
FIG. 15 illustrates differential counts for the dose response.
Figure 16:
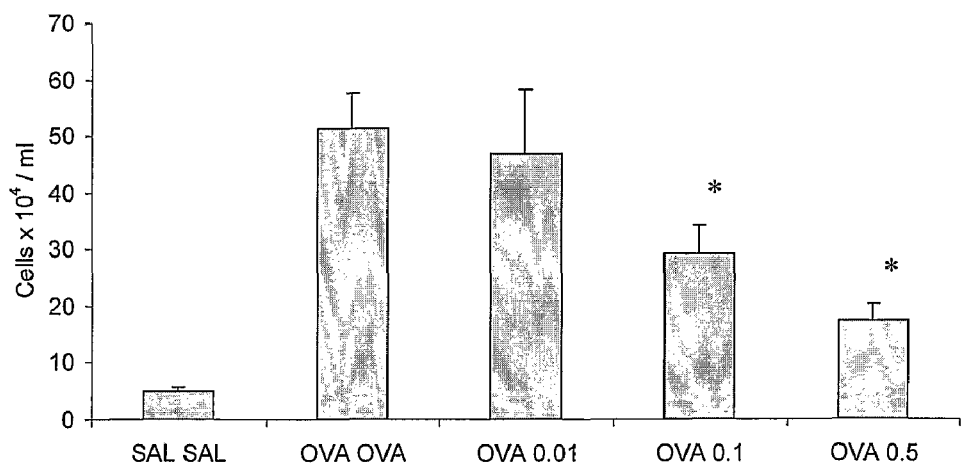
FIG. 16 illustrates the second dose response for the DMPP IP treatment effect on total cell accumulation in BAL of asthmatic mice.
Figure 17:
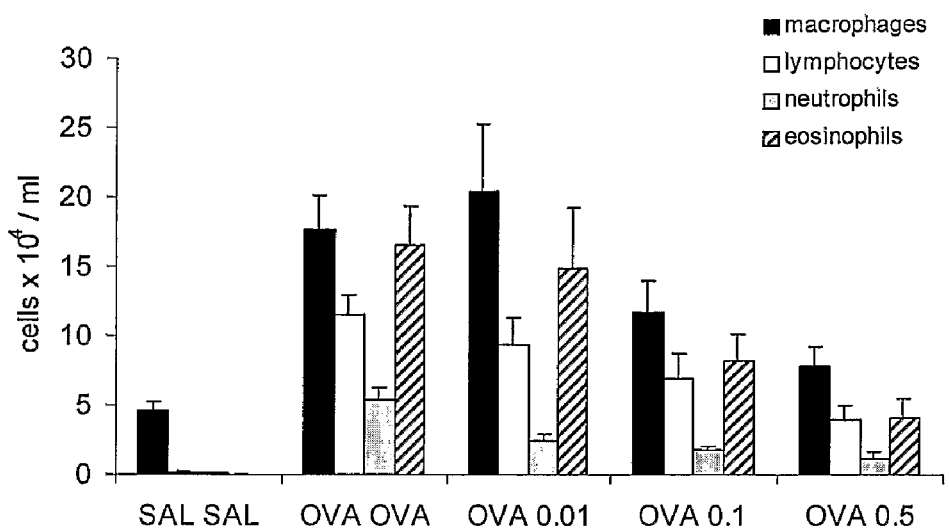
FIG. 17 illustrates differential counts from the second dose response.

OVA protein (chicken egg albumin; Sigma-Aldrich) emulsified in 2 mg aluminum hydroxide in PBS. After 4 weeks, challenge doses of 1.5%/50 μl OVA were administered intra-nasally. The challenge was performed daily for 3 consecutive days and then the mice assessed for allergic inflammation of the lungs 24 h after the last aerosol exposure. Groups of mice were treated with various concentrations of DMPP during the challenge period. Broncho-alveolar lavage (BAL) was performed and the fluid centrifuged at 400 g to separate cells from liquid. FIG. 14 shows that The number of cells was highly elevated in OVA challenged and non-treated mice. The DMPP treatment significantly reduced cell counts at the 0.5 and 2.0 mg/kg doses. FIG. 15 shows that the OVA challenged mice (OVA OVA) had more eoosinophils and lymphocytes in their BAL compared to the control group (sal sal). The DMPP treatment significantly reduced the presence of both osinophils and lymphocytes in BAL in all groups (n=8; p<0.05). FIG. 16 shows that he OVA challenged mice (OVA OVA) had more eoosinophils and lymphocytes in their BAL compared to the control group (sal sal). The DMPP treatment significantly reduced the presence of both osinophils and lymphocytes in BAL in all groups (n=8; p<0.05). FIG. 17 shows that The DMPP treatment significantly reduced eosinophil and lymphocyte counts in the 0.1 and 0.5 mg/kg doses, 0.5 mg/kg being the most effective dose for the anti-inflammatory effect of DMPP.

Figure 18:
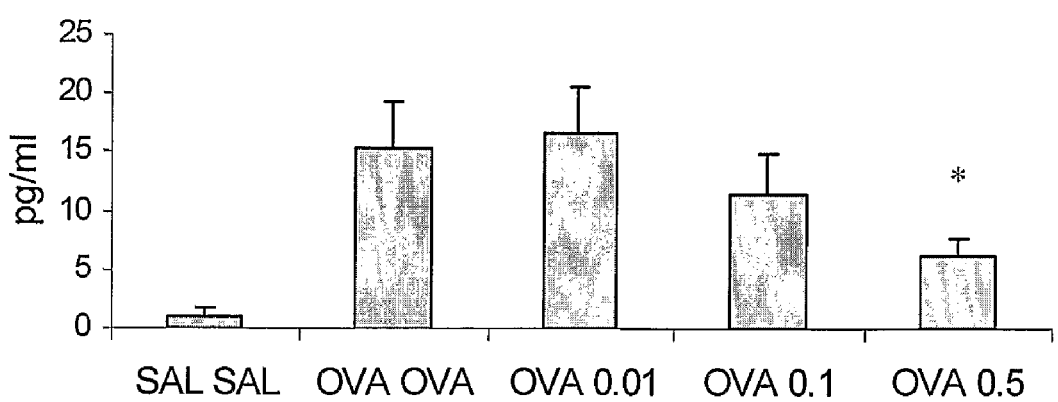
FIG. 18 illustrates BAL IL-5 levels from control, asthmatic and treated mice.

The supernatants were used to determine lung IL-5 levels. The total number of BAL cells and differential cell counts were evaluated. FIG. 18 shows that the OVA challenges increased IL-5 levels in BAL, while the DMPP treatment had a significant inhibitory effect on IL-5 levels in the 0.5 mg/kg treated-group of mice.

The experiment was repeated with the optimal dose of DMPP to assess the airway responsiveness.

Measurement of AHR

Airway hyper-reactivity (AHR) in response to metacholine was measured in anesthetized, tracheotomized, ventilated mice using a computer-controlled ventilator (FlexiVENT™).

Figure 19:
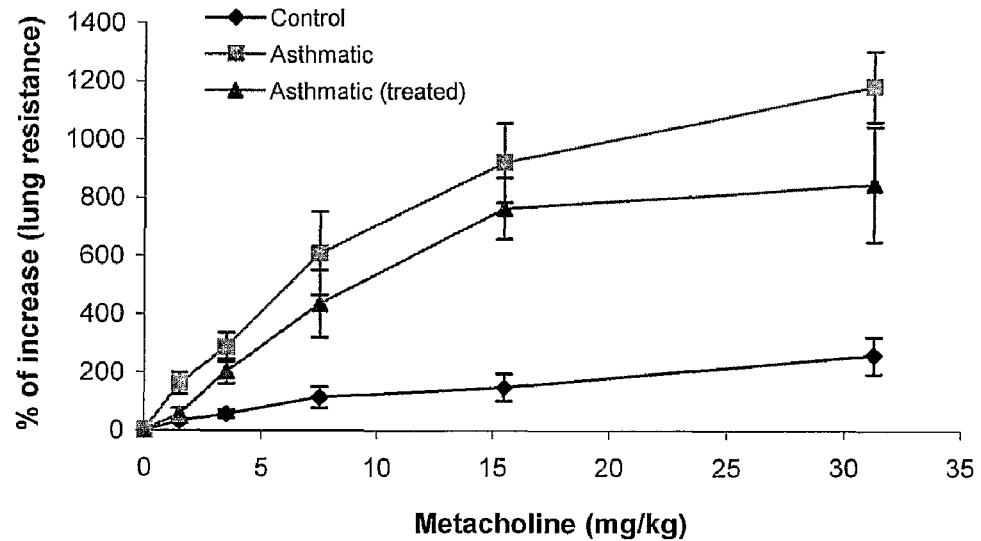
FIG. 19 illustrates lung resistance after metacholine challenges from normal, asthmatic and asthmatic treated with 0.5 mg/kg intranasal DMPP.
Figure 20:
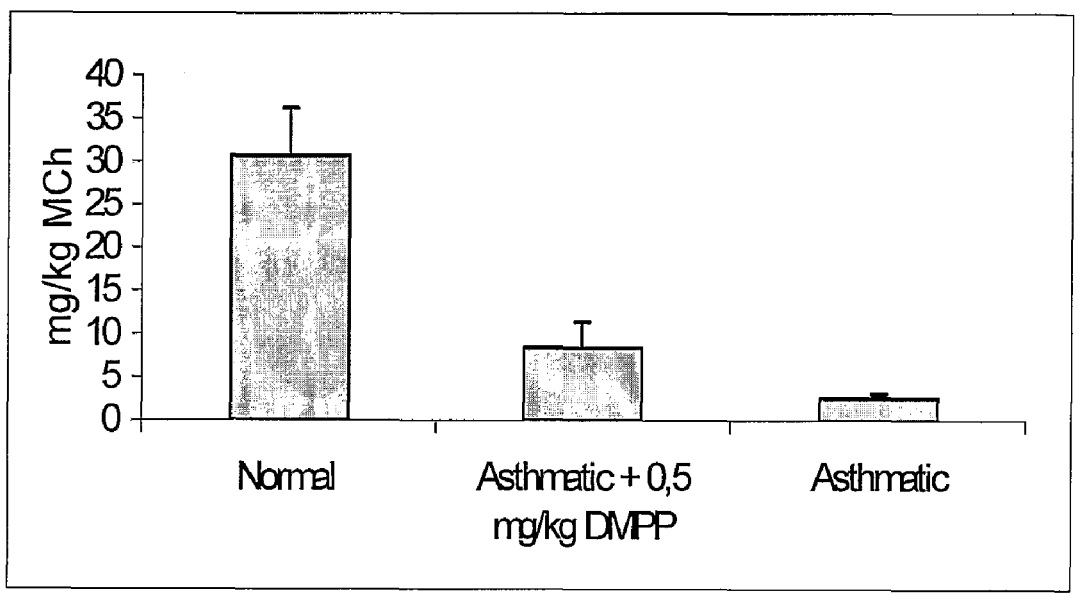
FIG. 20 illustrates a calculation of the provocative challenge dose of 200% lung resistance augmentation (PC 200)

Increasing doses of metacholine (0 mg/kg-32.5 mg/kg) were administered through the jugular vein. FIG. 19 shows that DMPP-reduced the % of augmentation of lung resistance compared to asthmatic mice. FIG. 20 shows that DMPP significantly reduced the PC200 in treated-mice compared to asthmatic mice (p=0.04; n=6).

Example VII

Effect of Agonist Treatment on mRNA Expression of IL-4.

Figure 21:
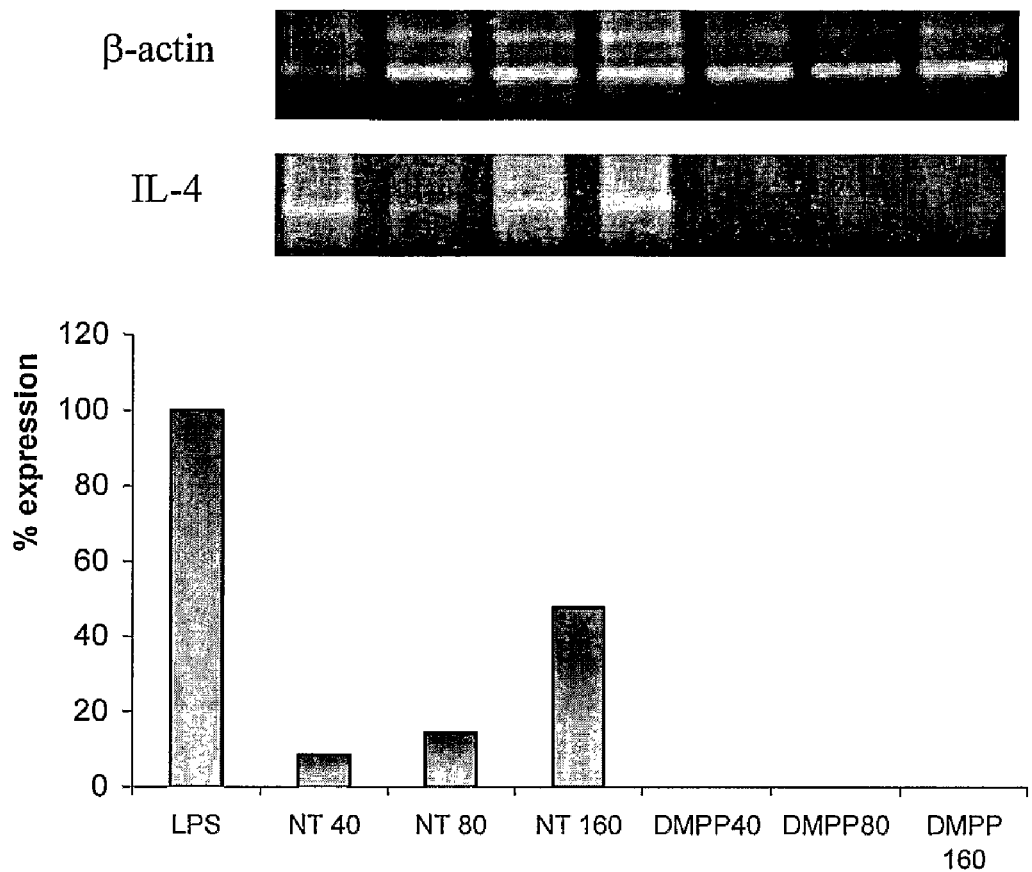
FIG. 21 illustrates IL-4 mRNA expression induced by a 24 h LPS stimulation.

The effect of agonist treatment on mRNA expression of IL-4, a cytokine that is well known to be involved in the development of asthma, was also tested (53). Nicotine decreased IL-4 mRNA expression by up to 92% with 40 μM (FIG. 9) DMPP completely blocked IL-4 mRNA expression. Reference is made to FIG. 21 which shows results expressed as described in FIG. 5. Cells were treated with different doses (40 to 160 μM for both nicotine and DMPP). The nicotine treatment induced a drop in the IL-4 mRNA expression (up to a 90% reduction of expression in the 40 μM group). As demonstrated previously, there was no IL-4 mRNA expression when cells were stimulated with SR antigen.

Example VIII

Action of Various Agonists on Eosinophil Transmigration.

To further investigate the down-regulatory effect of nicotinic agonists on inflammation in asthma, we tested the action of various agonists on eosinophil transmigration.

Figure 22:
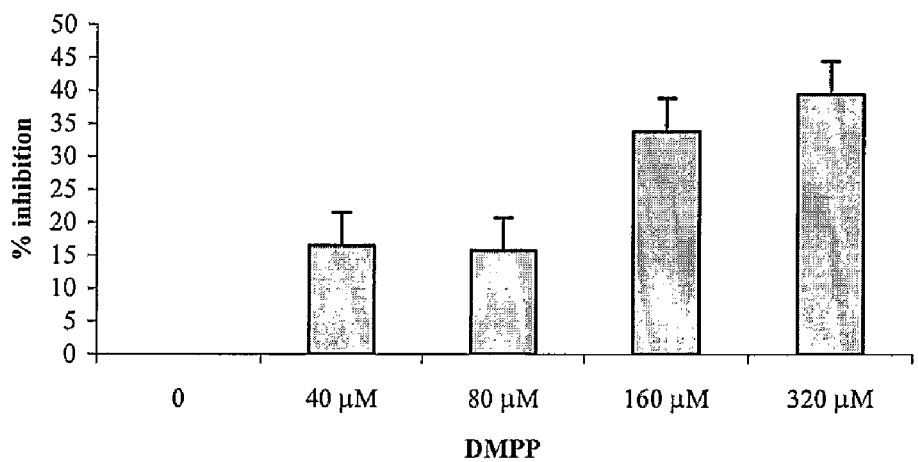
FIG. 22 illustrates the effect of DMPP on blood eosinophil transmigration.
Figure 23:
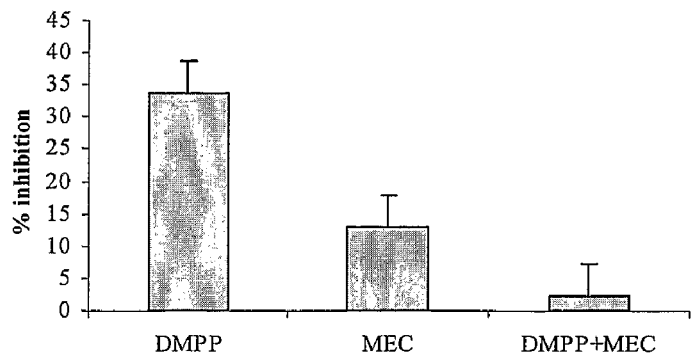
FIG. 23 illustrates the effect of mecamylamine, a nicotinic antagonist, on the inhibitory effect of DMPP on blood eosinophil transmigration.
Figure 24:
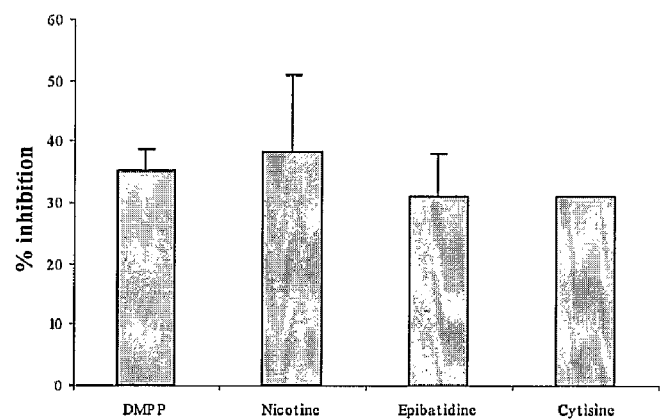
FIG. 24 illustrates the effect of additional nicotinic agonists (nicotine, epibatidine and cytisine) on transmigration of blood eosinophils.

Infiltration of eosinophils and other inflammatory cells into lung tissues is an important feature of asthma and the cause of airway inflammation and hyper-responsiveness. The passage of inflammatory cells from the circulation to the lung involves migration through the vascular endothelium, the basement membrane, and extra-cellular matrix components. Inflammatory cells cross the basement membrane by producing proteinases. In these preliminary in vitro experiments, the effects of various nicotinic agonists on the migration of purified blood eosinophils through an artificial basement membrane (Matrigel® coated chemotaxis chamber) were investigated. DMPP induced a dose-related inhibition of eosinophils transmigration (FIG. 22 shows that DMPP induces a dose-related inhibition of eosinophil transmigration across an artificial basement membrane.), while this effect was reversed by the antagonist mecamylamine (MEC) (FIG. 23 shows that mecamylamine reverses the effect of DMPP, suggesting that nicotinic receptor activation is necessary for the DMPP inhibitory effect). This inhibitory effect is further confirmed with other nicotinic agonists including nicotine, epibatidine and cytisine (FIG. 24) that all reduce blood eosinophil transmigration. Results are expressed as a percentage of inhibition (agonists-treated cells) compared to the control condition without the agonists.

These results suggest that nicotinic agonists down-regulate the synthesis or activation of proteinases that degrade basement membrane components, thus inhibiting the migration of eosinophils into lung mucosa.

Example IX

Effect of Nicotinic Agonists on Collagen Production.

Asthma is characterized by airway structural changes, including sub-epithelial collagen deposition, that may be a cause for the chronicity of the disease. An imbalance between collagen synthesis and its degradation by fibroblasts may be involved in this process (56). In preliminary experiments, we investigated the effects of nicotinic agonists on collagen A1 synthesis produced by primary normal fibroblasts. Collagen A1 gene expression was evaluated by RT-PCR.

The results are expressed percentage gene expression in agonists treated cells compared to non-treated cells.

Figure 25:
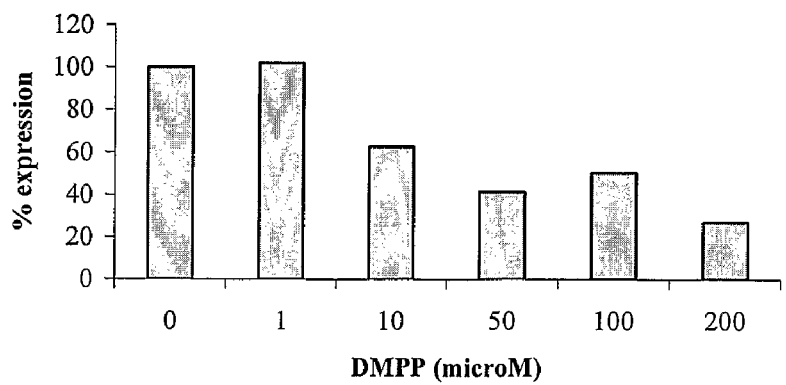
FIG. 25 illustrates the effect of DMPP on collagen 1A mRNA expression by normal human lung fibroblasts.
Figure 26:
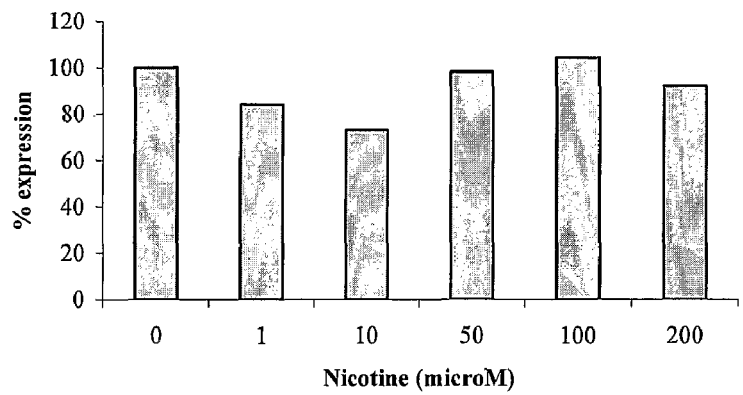
FIG. 26 illustrates the effect of nicotine on collagen 1A mRNA expression by human lung fibroblasts.
Figure 27:
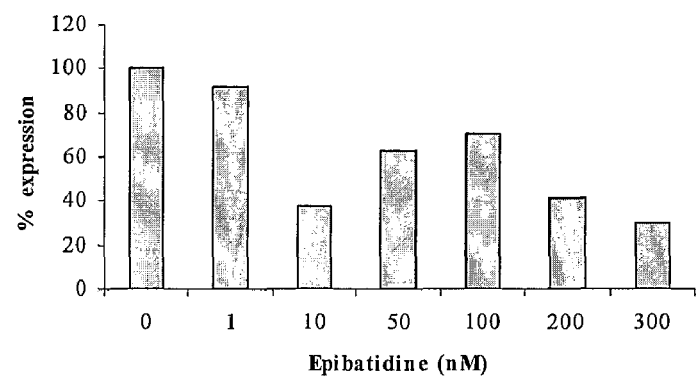
FIG. 27 illustrates the effect of epibatidine, another nicotinic agonist, on collagen 1A mRNA expression by human lung fibroblasts.

DMPP inhibits collagen A1 gene expression in a dose-dependent manner (FIG. 25). Nicotine has a slight inhibitory effect at 1 and 10 μM, whereas higher concentrations had no effects (FIG. 26), probably due to a desensitization of the receptors. Lower doses may be necessary to achieve an inhibition and will be tested. The inhibitory effect is also observed with epibatidine (FIG. 27).

Similar tests were carried out with the following analogues of DMPP and equivalent results were obtained.

Example X

Effects of DMPP Analogs

Based on our DMPP results, four (4) new DMPP analogs were developed and tested for their anti-inflammatory effects, improved hyper-responsiveness properties and smooth muscle-relaxing effects. Similarly to DMPP, ASM-002, ASM-003, ASM-004 and ASM-005 are synthetic agonists of nicotinic acetylcholine receptors. They are highly hydrophilic due to their quaternary salt structure, and therefore are not likely to cross easily the blood-brain barrier. Consequently they are less likely to induce addiction.

Example XI

Anti-Inflammatory Effects:

Effect of DMPP Analogs on Tumor Necrosis Factor (TNF) Release

Figure 28:
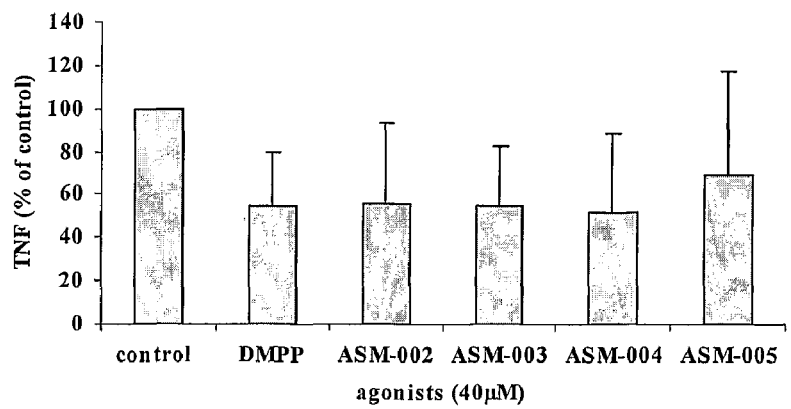
FIG. 28 illustrates the effect of DMPP, ASM-002, ASM-003, ASM-004, and ASM-005 on TNF release

Human monocytes were isolated from the blood of asthmatic patients by Ficoll-paque density gradient, let to adhere to tissue culture plates and stimulated with LPS (100 ng/ml) for 18 hours at 37° C. with or without increasing concentrations of nicotine. The release of TNF, a potent pro-inflammatory mediator, was measured in the cell culture supernatant by the ELISA method. Results are expressed as a percentage release from LPS-stimulated untreated cells (FIG. 28). Except for ASM-005, all analogs tested had an inhibitory effect on TNF release (n=8 to 10; p from 0.01 to 0.007).

Example XII

Effect of DMPP Analogs on Leukotriene C4 (LTC4) Production.

Blood eosinophils, the most increased inflammatory cells in asthma, were isolated by negative selection using bead-conjugated anti-CD16 monoclonal antibody and magnetic activating cell sorting. Cells were pre-incubated for 18 hours with the various DMPP analogs and then stimulated with 1 □M platelet-activating factor (PAF) to produce LTC4 which was measured by enzyme immunoassay.

The results indicate that 3 out of 4 analogs tested are able to down-regulate LTC4 release (Table 1).

TABLE 1

Effects of DMPP and analogs on LTC4 release.

|  | LTC4 pg/ml |
|---|---|
| — | 1725.80 |
| DMPP | 545.00 |
| ASM002 | 246.40 |
| ASM003 | 613.90 |
| ASM004 | 601.60 |

Example XIII

Smooth Muscle Relaxing Effects:

Effect of DMPP Analogs on Mouse Tracheal Airway Smooth Muscle Responsiveness.

Figure 29:
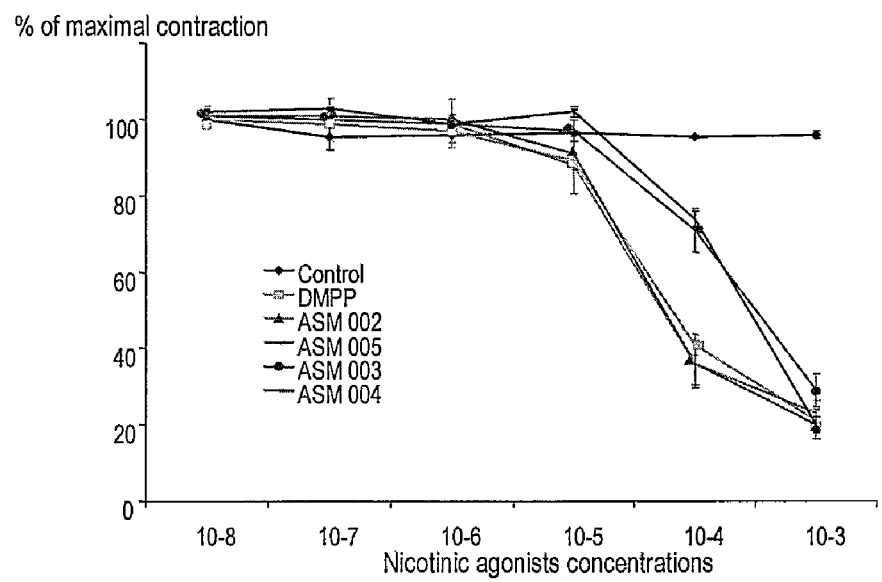
FIG. 29 illustrates the effect of DMPP, ASM-002, ASM-003, ASM-004, and ASM-005 on mouse tracheal airway smooth muscle responsiveness.

To demonstrate the relaxing effects of DMPP analogs on airway smooth muscle cells, isometric studies were performed on isolated mouse tracheas. Tracheal rings were mounted isometrically to force transducers in organ baths containing Krebs bicarbonate solution at 37° C. and bubbled with 95% $O_2$-5% $CO_2$, pre-contracted with submaximal concentration of metacholine ($10^{-5}$) and cumulative doses of the analogs were added to the baths. Changes of tension are recorded. Results are expressed as a percentage of maximal contraction (FIG. 29).

Similarly to DMPP, its analogs induced a dose dependant relaxation of tracheal smooth muscles pre-contracted with metacholine.

Overall these results indicated that ASM-002, ASM-003, ASM-004 and ASM-005 the new synthesized analogs presented similar anti-inflammatory and smooth-muscle relaxing effects as DMPP.

Example XIV

Mouse Model
Effects of ASM-002 on Lung Inflammation

Ovalbumin-sensitized mice (6=8) were challenged with the allergen and simultaneously treated intra-nasally with increasing concentrations of ASM-002 (0.5 to 4 mg/kg/d) for 3 days. The number of cells recovered by broncho-alveolar lavage was used as a measure of lung inflammation.

Figure 30:
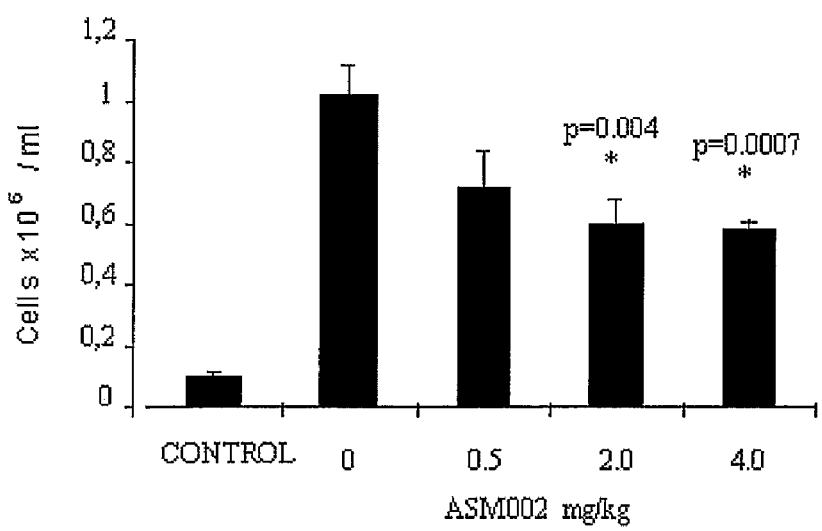
FIG. 30 illustrates the effect of ASM-002 on lung inflammation.

As shown in FIG. 30, ASM-002 significantly inhibits in a dose dependant manner the cellular inflammation in the lungs of asthmatic mice ($ED_{50}$=0.71 mg/kg, n=8).

Example XV

Mouse Model
Effects of ASM-002 on Lung Resistance in a Mouse Model of Asthma

Lung response to a broncho-constrictive agent, metacholine, was measured by a Flexi-vent® apparatus. Ovalbumin-sensitized animals were treated intra-nasally with ASM-002 (4 mg/kg) during 3 days and 10 minutes prior to the metacholine challenge and compared to untreated OVA-sensitized animals. A negative control group of un-sensitized animals and a positive control group that received Salbutamol (Ventolin) 10 minutes before the metacholine challenge were also included.

Figure 31:
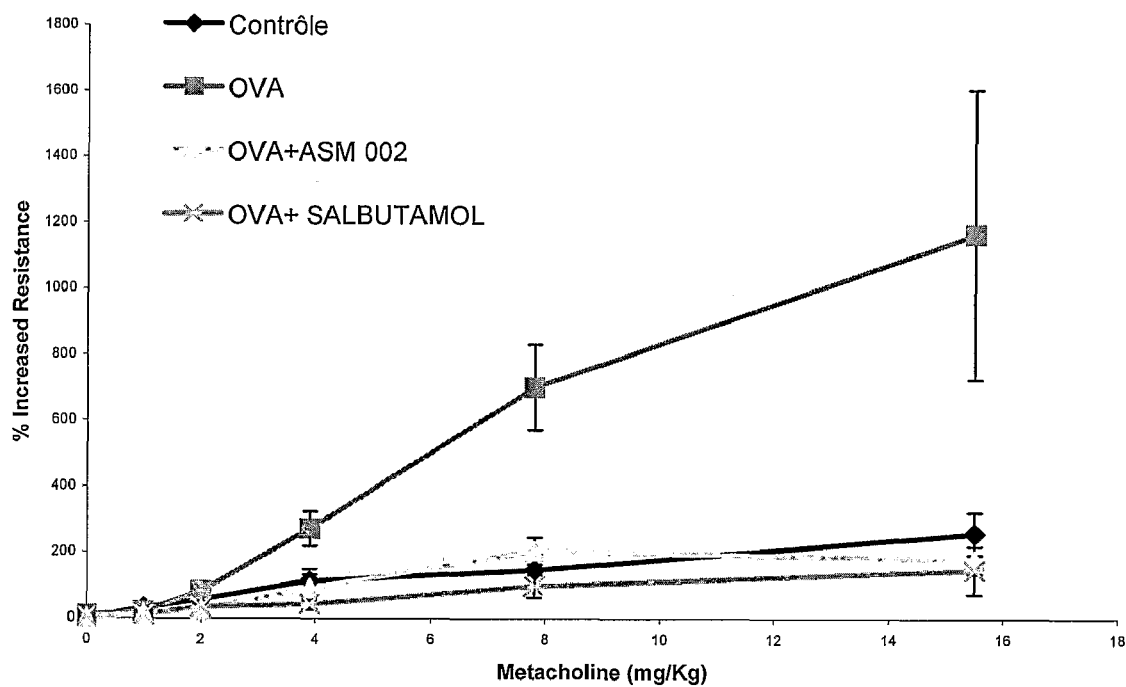
FIG. 31 illustrates the effects of ASM-002 on lung resistance in a mouse model of asthma.

The results show (FIG. 31) an increase in lung resistance, induced by metacholine, in OVA-sensitized mice compared to the negative control group. A significant reduction (return to baseline levels) in lung resistance is observed in ASM-002-treated mice compared to untreated mice (n=8, p<0.02). This effect is similar to that obtained with Salbutamol (Ventolin™), the most common brochodilator currently used in asthma to relieve broncho-constriction symptoms (n=4, p<0.02).

Example XVI

Dog Asthma Model

In this model 12 dogs naturally sensitized to the roundworm *Ascaris suum* were used in a cross-over study design. Four groups of 3 dogs were randomly formed, exposed to the allergen, and each animal was left either untreated or received alternatively, ASM-002 (4 mg/kg 2× day in the food), or prednisone (1 mg/kg 1× day in the food), the most commonly used corticosteroid drug used to treat inflammation in asthma. Comparative Effects of ASM-002 and Prednisone™ on Lung Inflammation Cellular inflammation was evaluated in the bronchoalveolar lavages.

Figure 32:
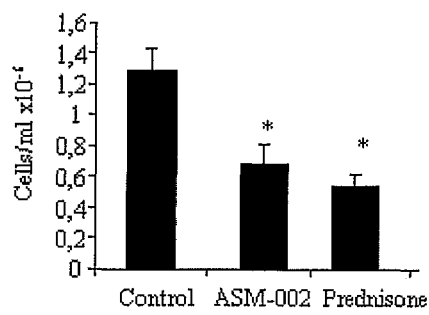
FIG. 32 illustrates the comparative effects of ASM-002 and prednisone on lung inflammation.

As shown in FIG. 32, ASM-002 (8 mg/kg) inhibits significantly the cellular inflammation in the lungs of asthmatic dogs with a similar efficacy as Prednisone™ the most frequently used anti-inflammatory drug (n=12, p<0.05).

Example XVII

Effects of ASM-002 in a Dog Model of Lung Hyper-Responsiveness.

Hyper-responsiveness is described as the capacity of the lung to react (to increase lung resistance) to a non-specific external stimuli like metacholine or to allergens. A hyper-responsive allergen-sensitized dog (asthmatic) will react to lower concentrations of metacholine compared to a non allergic dog. Similarly, improvement in lung hyper-responsiveness is shown by an increase in metacholine concentrations necessary to induce the same level of lung resistance.

Increasing concentrations of metacholine were administered with or without treatment with ASM-002 or Prednisone™ and lung resistance recorded.

Figure 33:
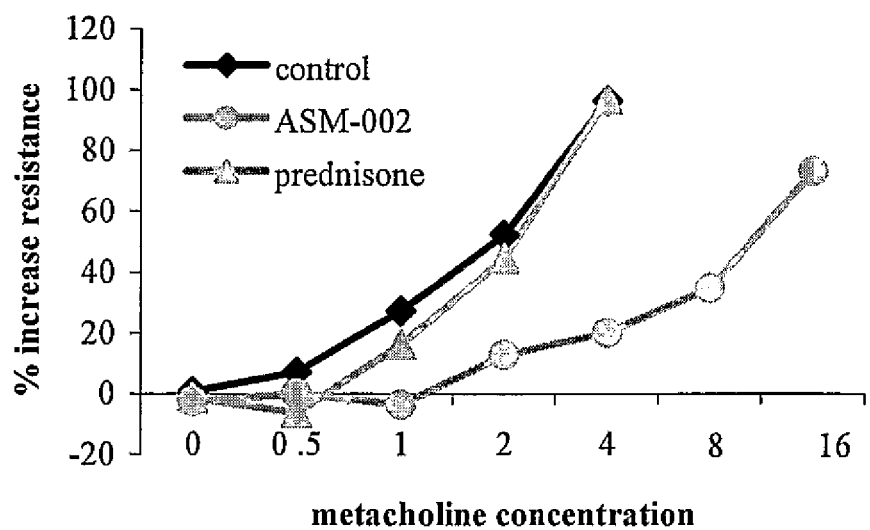
FIG. 33 illustrates the effects of ASM-002 in a dog model of lung hyper-responsiveness.

As shown in FIG. 33, ASM-002 decreased lung resistance in 7 out of 12 hyperresponsive dogs. None of the 12 dogs showed improved hyper-responsiveness with prednisone (p=0.005).

Example XVIII

Muscle-Relaxing Properties of ASM-002

Figure 34:
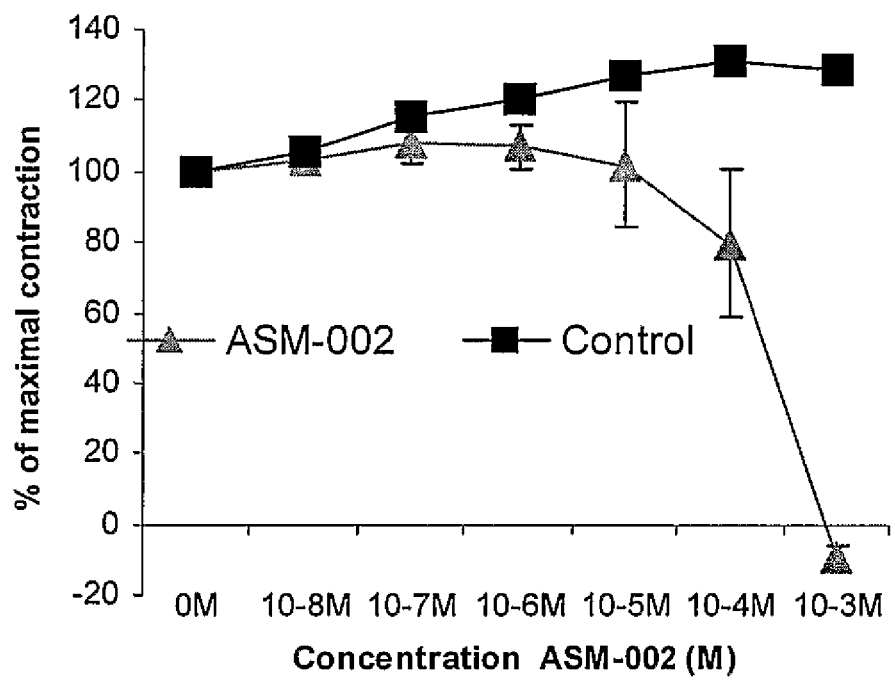
FIG. 34 illustrates the muscle-relaxing properties of ASM-002 on mouse tracheas.
Figure 35:
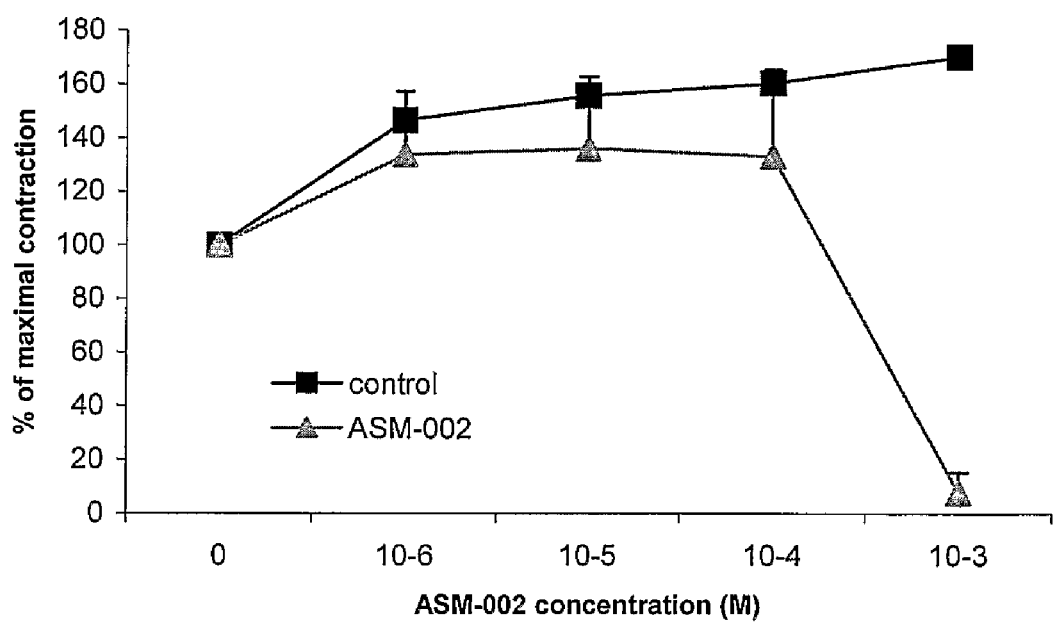
FIG. 35 illustrates the muscle-relaxing properties of ASM-002 on dog bronchial rings.
Figure 36:
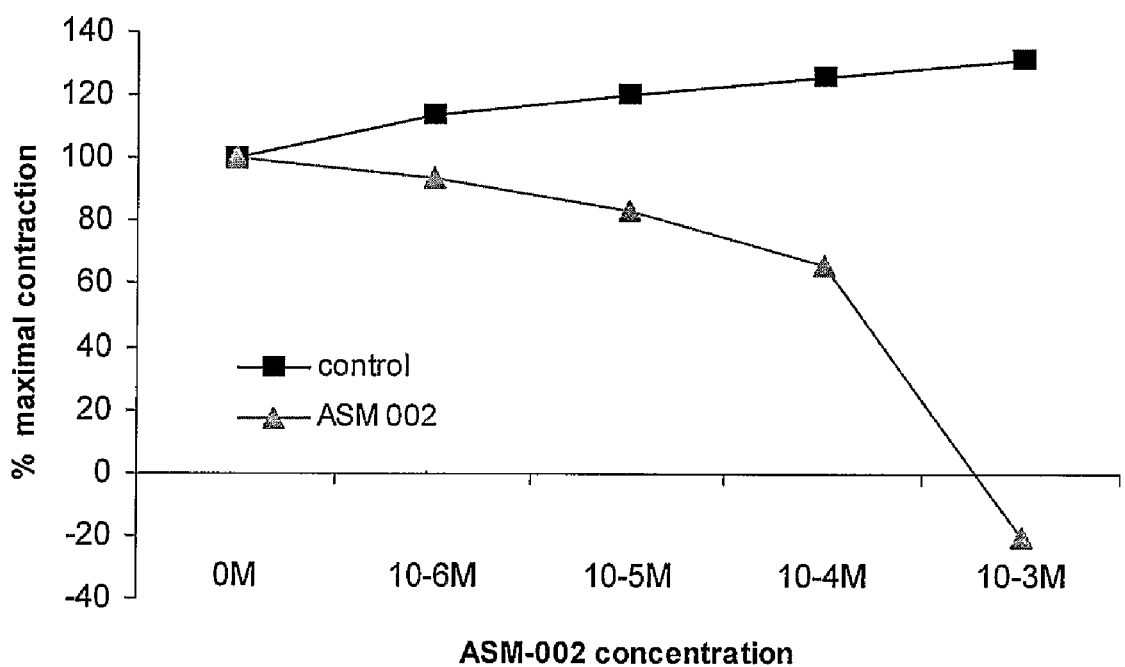
FIG. 36 illustrates the muscle-relaxing properties of ASM-002 on human bronchial rings.

To further demonstrate the relaxing effects of ASM-002 on airway smooth muscle cells, isometric studies were performed on isolated mouse tracheas, bronchial rings from dog's lungs and bronchial rings from resected human lungs. As described previously, tracheal or bronchial rings were mounted isometrically to force transducers in organ baths containing Krebs bicarbonate solution at 37° C. and bubbled with 95% $O_2$-5% $CO_2$, pre-contracted with submaximal concentration of metacholine cumulative doses of ASM-002 added. Changes of tension are recorded. Results are expressed as a percentage of maximal contraction for mouse (FIG. 34, p=0.002), dog (FIG. 35, p=0.004) and human (FIG. 36)

These results of examples XIV to XVIII showed that ASM-002 present a relaxing effect on pre-contracted mice tracheas, dog and human bronchi.

Example XX

In Vitro Studies.

Figure 37:
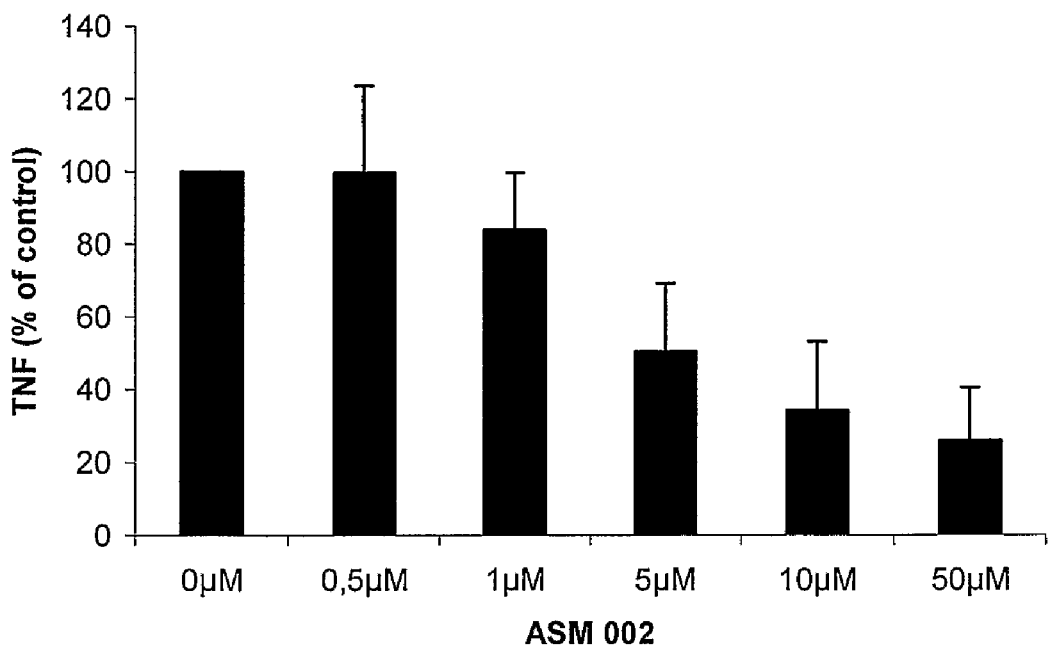
FIG. 37 illustrates the inhibitory effects of ASM-002 on potent inflammatory mediators release by human blood cells isolated from asthmatic patients.

The anti-inflammatory activity of ASM-002 was observed in vivo in mice and dogs in previous Examples. To further characterize this effect, the drug was tested for its capacity to inhibit the release of 2 potent inflammatory mediators by human blood cells isolated from asthmatic patients Tumor necrosis factor (TNF) is a mediator released in inflammatory states. Human blood monocytes were stimulated in vitro with lipopolysaccharide (LPS) to produce large amounts of TNF, increasing doses of ASM-002 were added and the levels of TNF were measured (FIG. 37, $EC_{50}$=3 µM, n=6, p=0.0045 at 5 µm, 0.0014 at 10 µm and 0.0003 at 50 µm). A dose-dependant inhibition of TNF release was observed with ASM-002

Example XXI

Comparative Effects of ASM-002 with DMPP and Dexamethasone on TNF Production by LPS-Stimulated Blood Monocytes.

Figure 38:
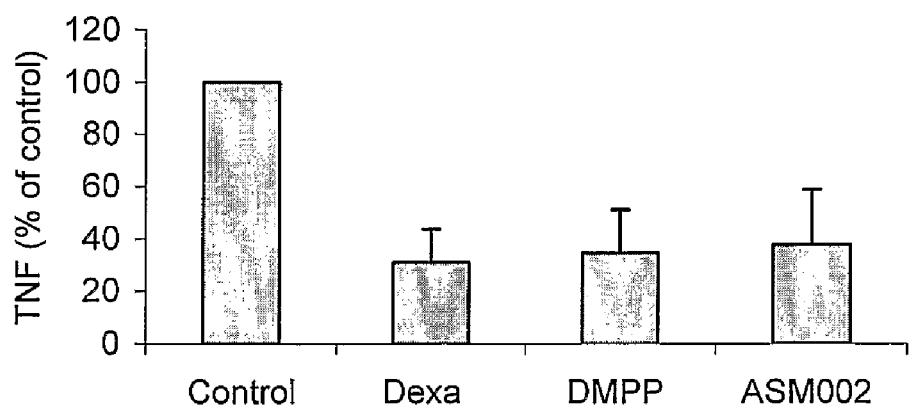
FIG. 38 illustrates the comparative effects of ASM-002 with DMPP and dexamethasone on TNF production by LPS-stimulated blood monocytes.

As shown in FIG. 38, results are expressed as a percentage from untreated control cells, all drugs were added at a 40 µM concentration and are the mean of 5 different experiments (5 subjects). ASM-002 inhibits TNF release from human blood monocytes as well as dexamethasone and DMPP (p=from 0.02 to 0.001)

Leukotriene $C_4$ ($LTC_4$) is a inflammatory lipid mediator highly produced in asthma, it is released in large amounts by blood eosinophils.

Human blood eosinophils were isolated from blood of asthmatic patients, stimulated in vitro with platelet activating factor (PAF) to produce large amounts of LTC4, and treated or not with 80 µM ASM-002.

Figure 39:
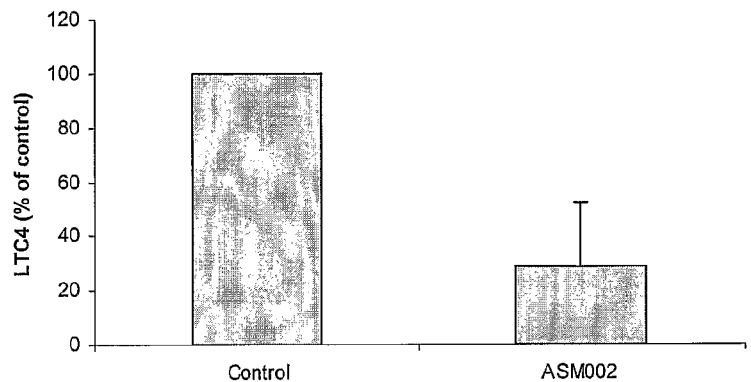
FIG. 39 illustrates the inhibition of LTC4 production by ASM-002.

A significant inhibition of LTC4 production by ASM-treated eosinophils was observed (FIG. 39, p=0.0007). The results represent an average of 6 different experiments (6 patients).

The results showed that ASM-002 present combined anti-inflammatory and broncho-dilating properties and improved hyperresponsiveness, which could be highly effective for the relief and treatment of asthma and other obstructive respiratory diseases.

Example XXII

Other Nicotinic Acetylcholine Receptor Analogs

Other analogs such as nicotine, cytisine and epibatidine as described herein can be used as nicotinic receptors inhibitors in the treatment of pulmonary inflammation.

Figure 40:
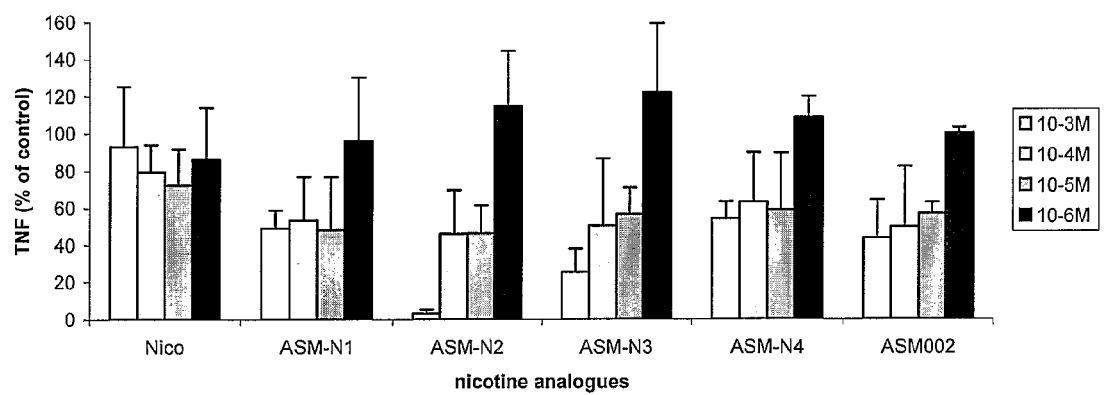
FIG. 40 illustrates the effect of nicotine, ASM-N1, ASM-N2, ASM-N3, ASM-N4 and ASM-002 on TNF production.

Anti-Inflammatory Effects:

Human blood monocytes were isolated by Ficoll-paque density gradient, let to adhere to tissue culture plates and stimulated with LPS (100 ng/ml) for 18 hours at 37° C. with or without increasing concentrations of nicotine analogues. The results obtained are disclosed in FIG. 40, significance levels are shown in Table 2.

TABLE 2

Significance levels of the effects of Nicotinic analogs on LPS stimulation.

| Concentration (M) | Nicotine p = | ASM-N1 p = | ASM-N2 p = | ASM-N3 p = | ASM-N4 p = |
|---|---|---|---|---|---|
| $10^{-4}$ | 0.034 | 0.011 | 0.006 | 0.037 | 0.035 |
| $10^{-5}$ | 0.032 | 0.015 | 0.001 | 0.008 | 0.039 |

A significant decrease of TNF release was observed with increasing concentrations of the four nicotine analogs.

Example XXIII

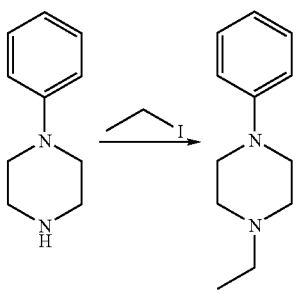

1-Phénylpipérazine (1 eq), iodoethane (1 eq), and sodium carbonate (2 eq) were mixed in tert-butanol. The mixture was refluxed for 20 hours. The mixture is then dissolved in chloroform and extracted with water three times. The organic layer was washed with 1N aqueous HCl solution three times. The aqueous layer was then basified to a basic pH with NaOH pellets. The basic aqueous layer was then extracted with chloroform three times and the combined organic extracts dried over $Na_2SO_4$ and evaporated to dryness. The crude product was purified using silica gel flash chromatography using a gradient of 0-5% MeOH in chloroform. The desired product was obtained as a yellow oil. (yield. 52%).

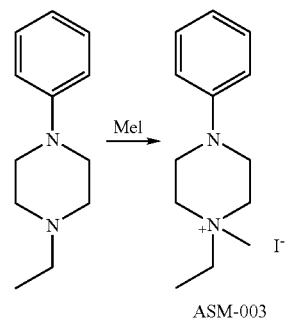

ASM-003

N-ethylphenylpipérazine (1 eq, 0.6 mmol) and iodomethane (excess >10 eq, 1 ml) were stirred in ether at room temperature for 4 days. The resulting white precipitate of ASM-003 was isolate by vacuum filtration. (yield 75%).

Example XXIV

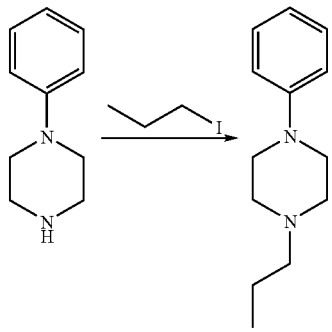

1-Phénylpiperazine (1 eq), iodopropane (1 eq), and sodium carbonate (2 eq) were mixed in tert-butanol. The mixture was refluxed for 20 hours. The mixture is then dissolved in chloroform and extracted with water three times. The organic layer was washed with 1N aqueous HCl solution three times. The aqueous layer was then basified to a basic pH with NaOH pellets. The basic aqueous layer was then extracted with chloroform three times and the combined organic extracts dried and evaporated to dryness. The crude product was purified using silica gel flash chromatography using a gradient of 0-5% MeOH in chloroform. The desired product was obtained as a yellow oil. (yield. 83%).

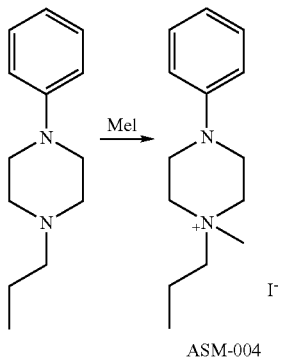

N-propylphenylpiperazine (1 eq, 0.6 mmol) and iodomethane (excess >10 eq, 1 ml) were mixed and stirred at room temperature in ether for 2 days. The mixture was then refluxed for 48 hours with an additional amount of iodomethane (>10 eq) with a (1:1) mixture of THF and ether. The mixture was evaporated and diluted in ether to yield a white precipitate of ASM-004 isolated by vacuum filtration. (yield 86%).

Example XXV

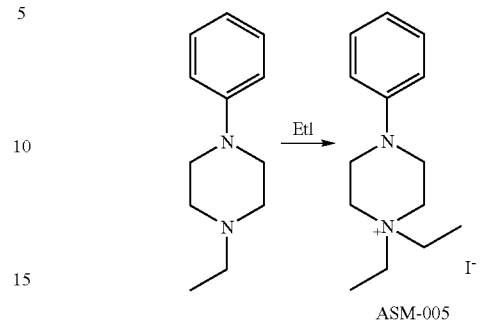

N-ethylphenylpiperazine prepared in example XXIII (1 eq, 0.5 mmol) and iodoethane (excess >10 eq, 1 ml) were stirred in ether at room temperature for 2 days. The mixture was then refluxed for 48 hours with an additional amount of iodoethane (>10 eq), with a (1:1) mixture of THF and ether. The mixture was evaporated and diluted in ether to yield a white precipitate of ASM-005 isolated by vacuum filtration (yield 62%).

or

N-ethylphenylpiperazine (1 eq, 3.94 mmol) and iodoethane (excess >10 eq, 3 ml) were stirred in acetonitrile at room temperature The mixture Was evaporated and diluted in ether to yield a white precipitate of ASM-005 isolated by vacuum filtration (yield 27%).

Example XXVI

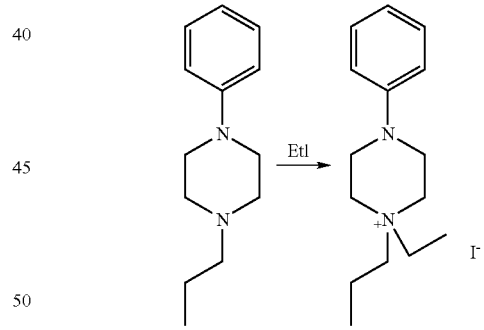

N-propylphenylpiperazine (1 eq, 0.51 mmol) and iodoethane (excess >10 eq, 1 ml) were stirred in ether at room temperature for 2 days The mixture was then refluxed for 48 hours with an additional amount of iodoethane (>10 eq), with a (1:1) mixture of THF and ether. The mixture was evaporated and diluted in ether to yield a white precipitate isolated by vacuum filtration (yield 11%).

or

N-propylphénylpipérazine (1 eq, 0.1 mmol) et l'iodoethane (excess >10 eq, 1 ml) were stirred in refluxing acetone for 24 hours. The mixture was evaporated and diluted in ether to yield a white precipitate isolated by vacuum filtration (yield 75%).

Example XXVII

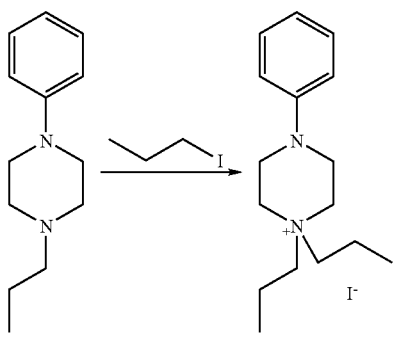

N-propylphenylpiperazine (1 eq, 0.53 mmol) and iodopropane (excess >10 eq, 1 ml) were stirred in ether at room temperature for 2 days The mixture was then refluxed for 48 hours with an additional amount of iodopropane (>10 eq, 1 ml), with a (1:1) mixture of THF and ether. The mixture was evaporated and diluted in ether to yield a white precipitate isolated by vacuum filtration (yield 10%).

Example XXVIII

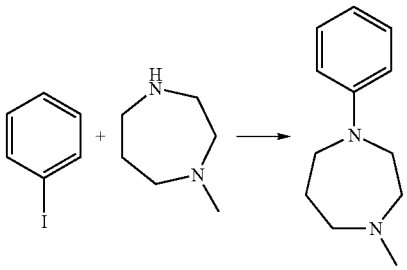

In a flame-dried round bottom flask under nitrogen, iodobenzene (1 eq, 1.47 mmol), N-methylhomopiperazine (1.2 eq, 1.76 mmol), ethylene glycol (2 eq, 2.94 mmol), CuI (5% mol) and K3PO4 (2 eq, 2.94 mmol) were suspended in isopropanol (3 ml). The mixture was refluxed with stirring for 17 hour's. The resulting mixture was cooled down to room temperature and water was added (5 ml). The mixture was extracted with ether (4×10 ml) and the combined organic extracts washed with brine, dried over Na2SO4 and evaporated to dryness under vacuum. The crude product was purified using silica gel flash chromatography using a gradient of 0% a 7.5% (2M NH3)MeOH in chloroform. The desired product was obtained as a yellow oil. (yield 64%).

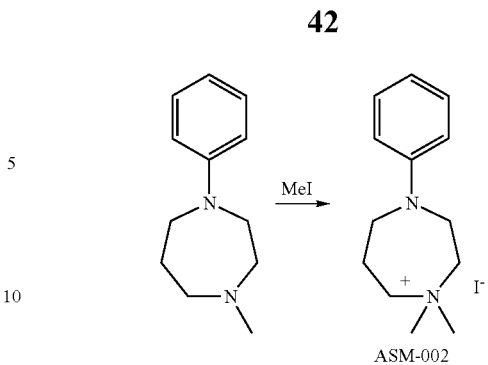

N-methylphenylhomopiperazine (1 eq, 0.36 mmol) and iodomethane (excess >10 eq, 1 ml) were stirred in ether at room temperature for 25 hours. The mixture was evaporated under vacuum, diluted with ether and the resulting white solid filtered under vacuum. 1,1-dimethyl-4-phenylhomopiperazinium iodide (Yield: 66%). Melting point: 158-160.

$^1$H NMR DMSO-d6 (ppm): (q, 2H) 7.18, (q, 2H) 6.74, (t, 1H) 6.64, (br s, 2H, 3.74), (m, 2H) 3.52, (m, 2H) 3.44, (t, 2H) 3.40, (s, 6H) 3.17, (bs s, 2H) 2.21.

$^{13}$C NMR DMSO-d6: 149, 129, 117, 112, 66, 65, 53, 47, 43, 22.

Example XXIX

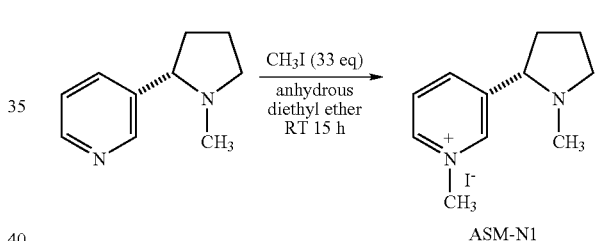

Nicotine (160 mg, 0.987 mmol) was dissolved in diethylether (5 ml), an excess of iodomethane (33 eq, 2 ml) was added and stirred in dark at room temperature over night for 15 hours.

The mixture was filtered under vacuum and the solid washed with diethylether. A white precipitate of ASM-N1 was obtained (yield 91%).

$^1$H NMR acetone-d6 (ppm): (m, 1H) 1.75, (m, 1H) 1.85, (m, 1H) 2.0, (s, 3H) 2.26, (m, 2H) 2.42, (m, 1H) 3.25 (t, 1H) 3.59, (s, 3H) 4.67 (t, 1H) 8.21, (d, 1H) 8.66, (d, 1H) 9.13, (s, 1H) 9.22.

Example XXX

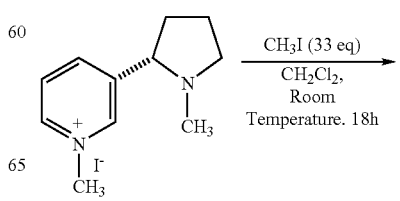

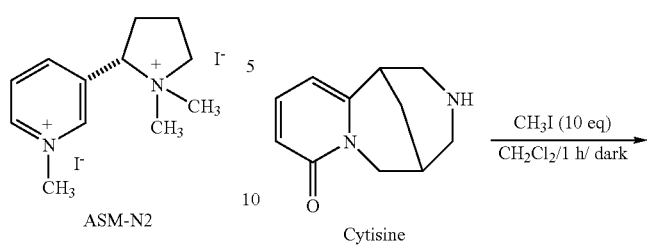

To the previously obtained nicotine salt compound (ASM-N1) (100 mg, 0.32 mmol) in anhydrous dichloromethane (15 ml) anhydre, was added an excess of iodomethane (33 eq, 0.64 ml) and stirred in dark at room temperature over night for 18 hours.

The mixture was filtered under vacuum and the solid washed with diethylether. A white precipitate was obtained (yield 26%).

$^1$H NMR acetone-d6 (ppm): (m, 3H) 2.26, (m, 1H) 2.71, (s, 3H) 2.82, (s, 3H) 3.14 (m, 1H) 3.76, (m, 1H) 3.86, (s, 3H) 4.40, (t, 1H) 5.04, (t, 1H) 8.31, (d, 1H), 8.85 (d, 1H), 9.17, (s, 1H) 9.31.

Example XXXI

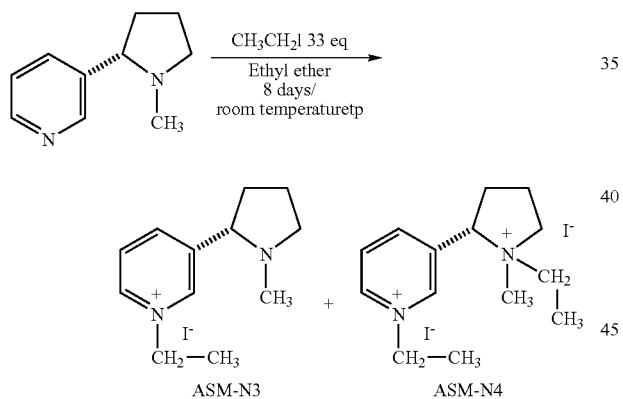

Nicotine (390 mg, 2.4 mmol) was dissolved in diethylether (10 ml), an excess of iodoethane (33 eq, 6.3 ml) was added and stirred in dark at room temperature for 7 days.

The solvent was evaporated and dichloromethane was added (100 ml) to cause precipitation of a white-yellowish of ASM-N4.

The organic layer was evaporated and the resulting oil washed with diethyl ether to yield ASM-N3.

$^1$H NMR acetone-d6 (ppm) of ASM-N3: (t, 3H) 1.70, (m, 1H) 1.82, (m, 1H) 1.95, (s, 3H), 2.26 (m, 3H) 2.43, (m, 1H) 3.30 (m, 1H) 3.70, (q, 2H) 4.95, (m, 1H) 8.20, (d, 1H) 8.69, (d, 1H) 9.29, (s, 1H) 9.39.

$^1$H NMR acetone-d6 (ppm) of ASM-N4: (2t, 3H) 1.2 et 1.5, (t, 3H) 1.75, (m, 1H) 1.85, (m, 2H) 2.05 (s, 3H) 2.41, (m, 1H) 2.71, (m, 2H) 3.45, (2q, 2H) 3.78 et 3.95, (m, 1H) 4.12, (q, 2H) 4.98, (m, 1H) 8.27, (d, 1H) 8.86, (d, 1H) 9.40, (s, 1H) 9.56

Example XXXII

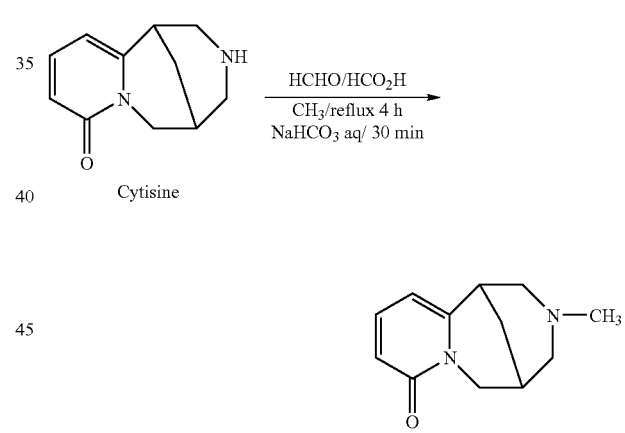

ASM-C1 was prepared using iodomethane (10 eq) in dichloromethane for 1 hour in dark in a manner similar to what is described in example XXIX. The caracterisation was consistent with the structure.

Example XXXIII

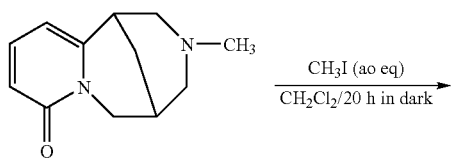

ASM-C2 was prepared using formaldehyde and formic acid in a similar manner as that described in J. Med. Chem. (2001), 44, 3946-3955. The characterisation was consistent with the structure.

Example XXXIV

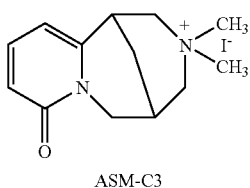

ASM-C3

ASM-C3 was prepared using iodomethane (40 eq) in dichloromethane for 20 hours i the dark in a manner similar to what is described in example XXIX. The characterisation was consistent with the structure.

Example XXXV

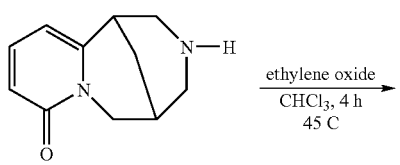

ASM-C4

ASM-C4 was prepared using ethylene oxyde in a similar manner as that described in II Farmaco 54 (1999) 438-451. The characterisation was consistent with the structure.

Example XXXVI

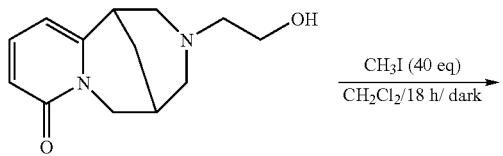

ASM-C5

ASM-05 was prepared using iodomethane (40 eq) in dichloromethane for 18 hours in the dark in a manner similar to what is described in example XXIX. The characterisation was consistent with the structure.

Example XXXVII

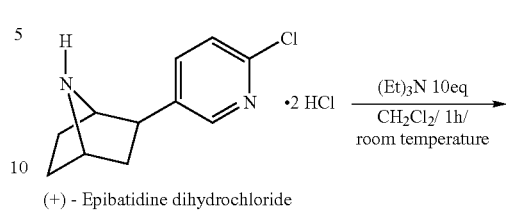

(+) - Epibatidine dihydrochloride → Epibatidine (+)—Epibatidine dihydrochloride was treated with triethyl amine (10 eq) in dichloromethane for 1 hour at room temperature and epibatidine was then isolated following standard isolation protocol.

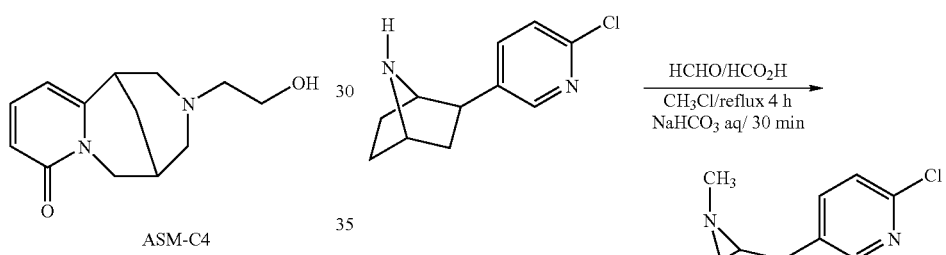

ASM-E1

ASM-E1 was prepared using epibatidine, formaldehyde and formic acid in a similar manner as that described in J. Med. Chem. 2001, 44, 3946-3955 The characterisation was consistent with the structure.

Example XXXVIII

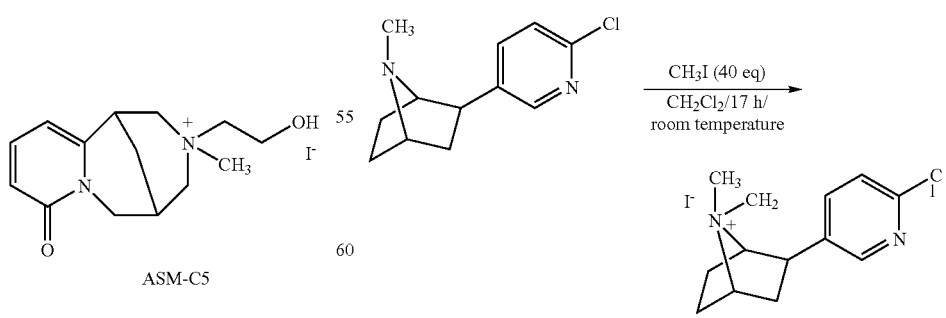

ASM-E2

ASM-E1 was prepared using iodomethane (40 eq) in dichloromethane for 17 hours at room temperature in a manner similar to what is described in example XXIX. The characterisation was consistent with the structure.

Although the present invention has been described herein above by way of preferred embodiments thereof, it can be modified, without departing from the spirit and nature of the subject invention as defined in the appended claims.

REFERENCES

1. Cormier, Y., J. Belanger, and P. Durand. 1985. Factors influencing the development of serum precipitins to farmer's lung antigen in Quebec dairy farmers. *Thorax* 40(2): 138-42.
2. Cormier, Y., L. Gagnon, F. Berube-Genest, and M. Fournier. 1988. Sequential bronchoalveolar lavage in experimental extrinsic allergic alveolitis. The influence of cigarette smoking. Am Rev Respir Dis 137(5):1104-9.
3. Cormier, Y., E. Israel-Assayag, G. Bedard, and C. Duchaine. 1998. Hypersensitivity pneumonitis in peat moss processing plant workers. Am J Respir Crit. Care Med 158(2): 412-7.
4. Gariepy, L., Y. Cormier, M. Laviolette, and A. Tardif. 1989. redictive value of bronchoalveolar lavage cells and serum precipitins in asymptomatic dairy farmers. Am Rev Respir Dis 140(5):1386-9.
5. Lawrence, E. C., T. B. Fox, R. B. Teague, K. Bloom, and R. K. Wilson. 1986. Cigarette smoking and bronchoalveolar T cell populations in sarcoidosis. Ann NY Acad Sci 465:657-64.
6. Valeyre, D., P. Soler, C. Clerici, J. Pre, J. P. Battesti, R. Georges, and A. J. Hance. 1988. Smoking and pulmonary sarcoidosis: effect of cigarette smoking on prevalence, clinical manifestations, alveolitis, and evolution of the disease. Thorax 43(7):516-24.
7. Rubin, D. T., and S. B. Hanauer. 2000. Smoking and inflammatory bowel disease. Eur J Gastroenterol Hepatol 12(8):855-62.
8. Thomas, G. A., J. Rhodes, J. T. Green, and C. Richardson. 2000. Role of smoking in inflammatory bowel disease: implications for therapy. Postgrad Med J 76(895):273-9.
9. Guslandi, M. 1999. Nicotine treatment for ulcerative colitis. Br J Clin Pharmacol 48(4):481-4.
10. Guslandi, M. 1999. Long-term effects of a single course of nicotine treatment in acute ulcerative colitis: remission maintenance in a 12-month follow-up study. Int J Colorectal Dis 14(4-5):261-2.
11. Rezvani, A. H., and E. D. Levin. 2001. Cognitive effects of nicotine. Biol Psychiatry 49(3):258-67.
12. Kelton, M. C., H. J. Kahn, C. L. Conrath, and P. A. Newhouse. 2000. The effects of nicotine on Parkinson's disease. Brain Cogn 43(1-3):274-82.
13. Bertram, K. G. 1998. Basic and clinical pharmacology. Editions Appelton and Lange. Stanford, Conn.
14. Sekhon, H. S., Y. Jia, R. Raab, A. Kuryatov, J. F. Pankow, J. A. Whitsett, J. Lindstrom, and E. R. Spindel. 1999. Prenatal nicotine increases pulmonary alpha7 nicotinic receptor expression and alters fetal lung development in monkeys. J Clin Invest 103(5):637-47.
15. Maus, A. D., E. F. Pereira, P. I. Karachunski, R. M. Horton, D. Navaneetham, K. Macklin, W. S. Cortes, E. X. Albuquerque, and B. M. Conti-Fine. 1998. Human and rodent bronchial epithelial cells express functional nicotinic acetylcholine receptors. Mol Pharmacol 54(5):779-88.
16. Shriver, S. P., H. A. Bourdeau, C. T. Gubish, D. L. Tirpak, A. L. Davis, J. D. Luketich, and J. M. Siegfried. 2000. Sex-specific expression of gastrin-releasing peptide receptor: relationship to smoking history and risk of lung cancer. J Natl Cancer Inst 92(1):24-33.
17. Ferguson, D. G., M. A. Haxhiu, A. J. To, B. Erokwu, and I. A. Dreshaj. 2000. The alpha3 subtype of the nicotinic acetylcholine receptor is expressed in airway-related neurons of the nucleus tractus solitarius, but is not essential for reflex bronchoconstriction in ferrets. Neurosci Lett 287(2): 141-5.
18. Singh, S. P., R. Kalra, P. Puttfarcken, A. Kozak, J. Tesfaigzi, and M. L. Sopori. 2000. Acute and chronic nicotine exposures modulate the immune system through different pathways. Toxicol Appl Pharmacol 164(1):65-72.
19. Kalra, R., S. P. Singh, S. M. Savage, G. L. Finch, and M. L. Sopori. 2000. Effects of cigarette smoke on immune response: chronic exposure to cigarette smoke impairs antigen-mediated signaling in T cells and depletes IP3-sensitive Ca(2+) stores. J Pharmacol Exp Ther 293(1):166-71.
20. Sugano, N., K. Shimoda, K. Ito, and S. Murai. 1998. Nicotine inhibits the production of inflammatory mediators in U937 cells through modulation of nuclear factor-kappaB activation. Biochem Biophys Res Commun 252 (1):25-8.
21. Yates, S. L., M. Bencherif, E. N. Fluhler, and P. M. Lippiello. 1995. Up-regulation of nicotinic acetylcholine receptors following chronic exposure of rats to mainstream cigarette smoke or alpha 4 beta 2 receptors to nicotine. Biochem Pharmacol 50(12):2001-8.
22. Sopori, M. L., and W. Kozak. 1998. Immunomodulatory effects of cigarette smoke. J Neuroimmunol 83(1-2):148-56.
23. Lahmouzi, J., F. Simain-Sato, M. P. Defresne, M. C. De Pauw, E. Heinen, T. Grisar, J. J. Legros, and R. Legrand. 2000. Effect of nicotine on rat gingival fibroblasts in vitro. Connect Tissue Res 41(1):69-80.
24. Geng, Y., S. M. Savage, S. Razanai-Boroujerdi, and M. L. Sopori. 1996. Effects of nicotine on the immune response. II. Chronic nicotine treatment induces T cell anergy. Immunol 156(7):2384-90.
25. McCrea, K. A., J. E. Ensor, K. Nall, E. R. Bleecker, and J. D. Hasday. 1994. Altered cytokine regulation in the lungs of cigarette smokers. Am J Respir Crit. Care Med 150(3): 696-703.
26. Ohta, T., N. Yamashita, M. Maruyama, E. Sugiyama, and M. Kobayashi. 1998. Cigarette smoking decreases interleukin-8 secretion by human alveolar macrophages. Respir Med 92(7):922-7.
27. Suzuki, N., S. Wakisaka, Y. Takeba, S. Mihara, and T. Sakane. 1999. Effects of cigarette smoking on Fas/Fas ligand expression of human lymphocytes. Cell Immunol 192(1):48-53.
28. Zia, S., A. Ndoye, V. T. Nguyen, and S. A. Grando. 1997. Nicotine enhances expression of the alpha 3, alpha 4, alpha 5, and alpha 7 nicotinic receptors modulating calcium metabolism and regulating adhesion and motility of respiratory epithelial cells. Res Commun Mol Pathol Pharmacol 97(3):243-62.
29. Zhang, S., and T. M. Petro. 1996. The effect of nicotine on murine CD4 T cell responses. Int J Immunopharmacol 18(8-9):467-78.
30. Bugeon, L., and M. J. Dallman. 2000. Costimulation of T cells. Am J Respir Crit. Care Med 162(4 Pt 2):S164-8.
31. Green, J. M. 2000. The B7/CD28/CTLA4 T-cell activation pathway. Implications for inflammatory lung disease. Am J Respir Cell Mol Biol 22(3):261-4.
32. Lenschow, D. J., T. L. Walunas, and J. A. Bluestone. 1996. CD28/B7 system of T cell costimulation. Annu Rev Immunol 14:233-58.
33. Walunas, T. L., and J. A. Bluestone. 1998. CTLA-4 regulates tolerance induction and T cell differentiation in vivo. J Immunol 160(8):3855-60.

34. Walunas, T. L., D. J. Lenschow, C. Y. Bakker, P. S. Linsley, G. J. Freeman, J. M. Green, C. B. Thompson, and J. A. Bluestone. 1994. CTLA-4 can function as a negative regulator of T cell activation. Immunity 1(5):405-13.
35. Israel-Assayag, E., A. Dakhama, S. Lavigne, M. Laviolette, and Y. Cormier. 1999. Expression of costimulatory molecules on alveolar macrophages in hypersensitivity pneumonitis. Am J Respir Crit. Care Med 150(6):1830-4.
36. Israel-Assayag, E., M. Fournier, and Y. Cormier. 1999. Blockade of T cell costimulation by CTLA4-Ig inhibits lung inflammation in murine hypersensitivity pneumonitis. J Immunol 163(12):6794-9.
37. Larche, M., S. J. Till, B. M. Haselden, J. North, J. Barkans, C. J. Corrigan, A. B. Kay, and D. S. Robinson. 1998. Costimulation through CD86 is involved in airway antigen-presenting cell and T cell responses to allergen in atopic asthmatics. J Immunol 161(11):6375-82.
38. Mathur, M., K. Herrmann, Y. Qin, F. Gulmen, X. Li, R. Krimins, J. Weinstock, D. Elliott, J. A. Bluestone, and P. Padrid. 1999. CD28 interactions with either CD80 or CD86 are sufficient to induce allergic airway inflammation in mice. Am J Respir Cell Mol Biol 21(4):498-509.
39. Nicod, L. P., and P. Isler. 1997. Alveolar macrophages in sarcoidosis coexpress high levels of CD86 (B7.2), CD40, and CD30L. Am J Respir Cell Mol Biol 17(1):91-6.
40. Kesingland, A. C., C. T. Gentry, M. S. Panesar, M. A. Bowes, J. M. Vernier, R. Cube, K. Walker, and L. Urban. 2000. Analgesic profile of the nicotinic acetylcholine receptor agonists, (+)—epibatidine and ABT-594 in models of persistent inflammatory and neuropathic pain. Pain 86(1-2):113-8.
41. Mellon, R. D., and B. M. Bayer. 1999. The effects of morphine, nicotine and epibatidine on lymphocyte activity and hypothalamic-pituitary-adrenal axis responses. J Pharmacol Exp Ther 288(2):635-42.
42. Yokotani, K., M. Wang, S. Okada, Y. Murakami, and M. Hirata. 2000. Characterization of nicotinic acetylcholine receptor-mediated noradrenaline release from the isolated rat stomach. Eur J Pharmacol 402(3):223-9.
43. Yost, C. S., and B. D. Winegar. 1997. Potency of agonists and competitive antagonists on adult- and fetal-type nicotinic acetylcholine receptors. Cell Mol Neurobiol 17(1): 35-50.
44. Fecho, K., K. A. Maslonek, L. A. Dykstra, and D. T. Lysle. 1993. Alterations of immune status induced by the sympathetic nervous system: immunomodulatory effects of DMPP alone and in combination with morphine. Brain Behav Immun 7(3):253-70.
45. Thompson, D. C., R. J. Altiere, and L. Diamond. 1990. Nicotinic agonist modulation of feline bronchomotor tone. Clin Exp Pharmacol Physiol 17(2):83-97.
46. Barnes P J. 2001. Future Advances in COPD Therapy. Respiration 68(5):441-8.
47. Lasky J A and Ortiz, L A. 2001. Antifibrotic therapy for the treatment of pulmonary fibrosis. Am J Med Sci 322(4): 213-21.
48. Baron, J. A. 1996. Beneficial effects of nicotine and cigarette smoking: the real, the possible and the spurious. Br Med Bull 52(1):58-73.
49. Waldum, H. L., O. G. Nilsen, T. Nilsen, H. Rorvik, V. Syversen, A. K. Sanvik, O. A. Haugen, S. H. Torp, and E. Brenna. 1996. Long-term effects of inhaled nicotine. Life Sci 58(16):1339-46.
50. Warren, C. P. 1977. Extrinsic allergic alveolitis: a disease commoner in non-smokers. Thorax 32(5):567-9.
51. Cormier, Y., G. M. Tremblay, M. Fournier, and E. Israel-Assayag. 1994. Long-term viral enhancement of lung response to Saccharopolyspora rectivirgula. Am J Respir Crit. Care Med 149(2 Pt 1):490-4.
52. Gudmundsson, G., and G. W. Hunninghake. 1997. Interferon-gamma is necessary for the expression of hypersensitivity pneumonitis. J Clin Invest 99(10):2386-90.
53. , Denis, M., M. Bedard, M. Laviolette, and Y. Cormier. 1993. A study of monokine release and natural killer activity in the bronchoalveolar lavage of subjects with farmer's lung. Am Rev Respir Dis 147(4):934-9.
54. Wahlstrom, J., K. Katchar, H. Wigzell, O. Olerup, A. Eklund, and J. Grunwald. 2001. Analysis of intracellular cytokines in cd4(+) and cd8(+) lung and blood t cells in sarcoidosis. Am J Respir Crit. Care Med 163(1):115-21.
55. Cohn, L., C. Herrick, N. Niu, R. Homer, and K. Bottomly. 2001. IL-4 promotes airway eosinophilia by suppressing IFN-gamma production: defining a novel role for IFN-gamma in the regulation of allergic airway inflammation. J Immunol 166(4):2760-7.
56. Laliberte R., Rouabhia M, Bosse M, Chakir J. 2001. Decreased capacity of asthmatic bronchial fibroblasts to degrade collagen. Matrix Biol Jan; 19(8): 743-53.
57. Boulet, L. P., H. Turcotte, M. Laviolette, F. Naud, M. C. Bernier, S. Martel, and J. Chakir. 2000. Airway hyperresponsiveness, inflammation, and subepithelial collagen deposition in recently diagnosed versus long-standing mild asthma. Influence of inhaled corticosteroids. Am J Respir Crit. Care Med 162(4 Pt 1):1308-13.
58. Dempsey, O. J. 2000. Leukotriene receptor antagonist therapy. Postgrad Med J 76(902):767-73.
59. Busse, W. W. 1998. Leukotrienes and inflammation. Am J Respir Crit. Care Med 157(6 Pt 2):S210-3; discussion 5247-8.
60. Zisman, D. A., J. P. Lynch, G. B. Toews, E. A. Kazerooni, A. Flint, and F. J. Martinez. 2000. Cyclophosphamide in the treatment of idiopathic pulmonary fibrosis: a prospective study in patients who failed to respond to corticosteroids. Chest 117(6):1619-26.
61. Redington, A. E. 2000. Fibrosis and airway remodelling. Clin Exp Allergy 30 Suppl 1:42-5.
62. Frew, A. J., and Plummeridge M J. 2001. Alternative agents in asthma. J Allergy Clin Immunol 108(1):3-10.

We claim:
1. A compound of formula:

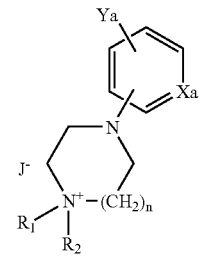

wherein
R$_1$ and R$_2$ are independently selected from the group consisting of methyl, ethyl, n-propyl and i-propyl,
Ya is hydrogen,
Xa is CH,
n is 2, and
J is a sulfonate.

* * * * *